(12) United States Patent
Hirota

(10) Patent No.: US 7,905,838 B2
(45) Date of Patent: Mar. 15, 2011

(54) IMAGE DIAGNOSTIC SYSTEM AND APPARATUS, AND PROCESSING METHOD THEREFOR

(75) Inventor: Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 716 days.

(21) Appl. No.: 11/727,925

(22) Filed: Mar. 29, 2007

(65) Prior Publication Data
US 2007/0244391 A1 Oct. 18, 2007

(30) Foreign Application Priority Data

Mar. 31, 2006 (JP) .................................. 2006-099926

(51) Int. Cl.
*A61B 8/00* (2006.01)
*A61B 8/14* (2006.01)
*A61B 6/00* (2006.01)
(52) U.S. Cl. .................... 600/445; 600/463; 600/476
(58) Field of Classification Search .................. 600/407
See application file for complete search history.

(56) References Cited

U.S. PATENT DOCUMENTS

| 5,321,501 A | 6/1994 | Swanson et al. |
| 2005/0256402 A1* | 11/2005 | Kawashima et al. ......... 600/437 |
| 2006/0100489 A1* | 5/2006 | Pesach et al. ................. 600/310 |

FOREIGN PATENT DOCUMENTS

| JP | 06-343637 | * 12/1994 |
| JP | 6-343637 A | 12/1994 |
| JP | 2001-079007 A | 3/2001 |

* cited by examiner

*Primary Examiner* — Eric F Winakur
*Assistant Examiner* — Hien Nguyen
(74) *Attorney, Agent, or Firm* — Buchanan Ingersoll & Rooney PC

(57) ABSTRACT

An image diagnostic system controls a probe to perform radial scanning within a body cavity produces data based on signals received by the probe to construct and display a tomographic image of the body cavity and surrounding biotissue. The system includes a generation unit, a selection unit and a conversion unit. The generation unit generates and outputs synchronization signals in synchronization with a timing of acquisition cycles of line units of the signals and generated at a higher frequency than output signals outputted corresponding to rotational angles of the probe upon performing the scanning. The selection unit successively receives the output signals, and selects and outputs first ones of the synchronization signals as received subsequent to the receptions of the output signals. Responsive to successive inputs of the synchronization signals selected by the selection unit, the conversion unit converts the reflected signals into digital signals and outputs the digital signals.

13 Claims, 21 Drawing Sheets

FIG. 7
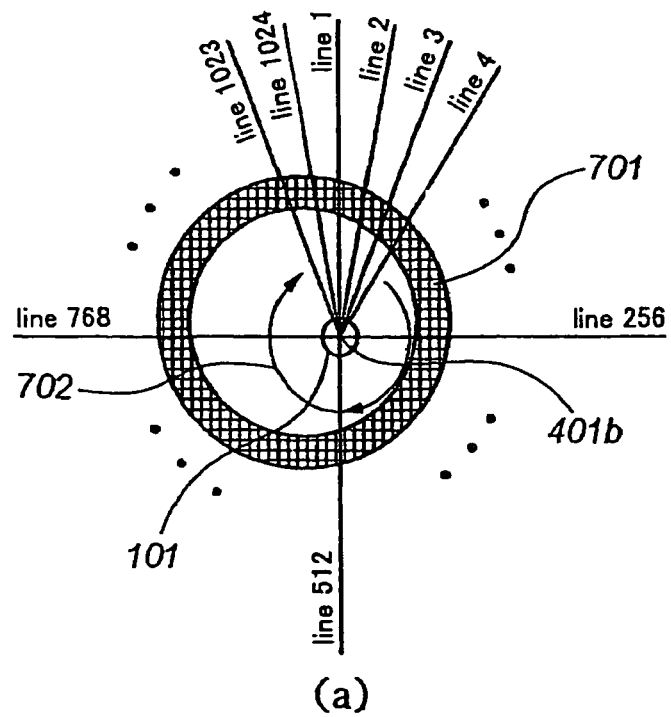
(a)
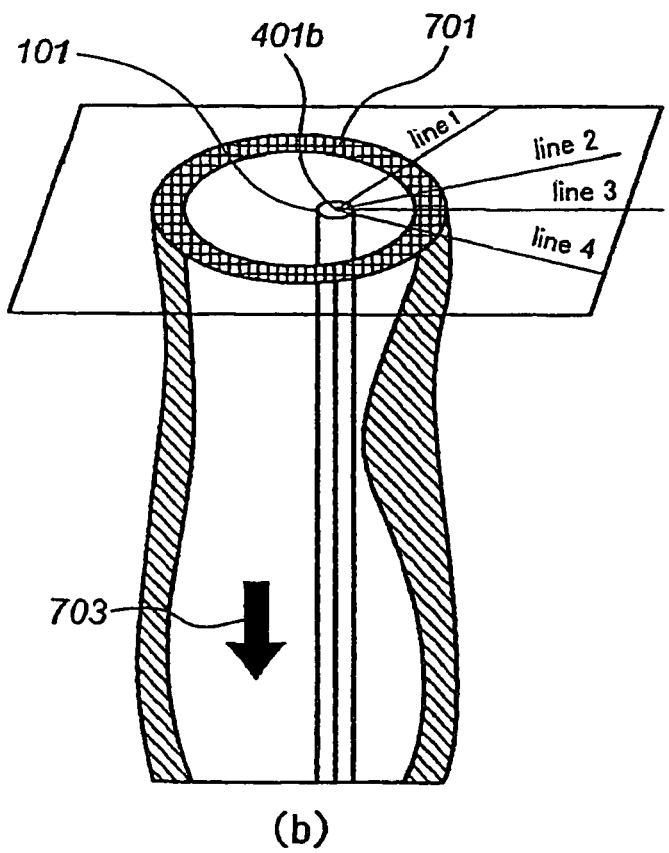
(b)

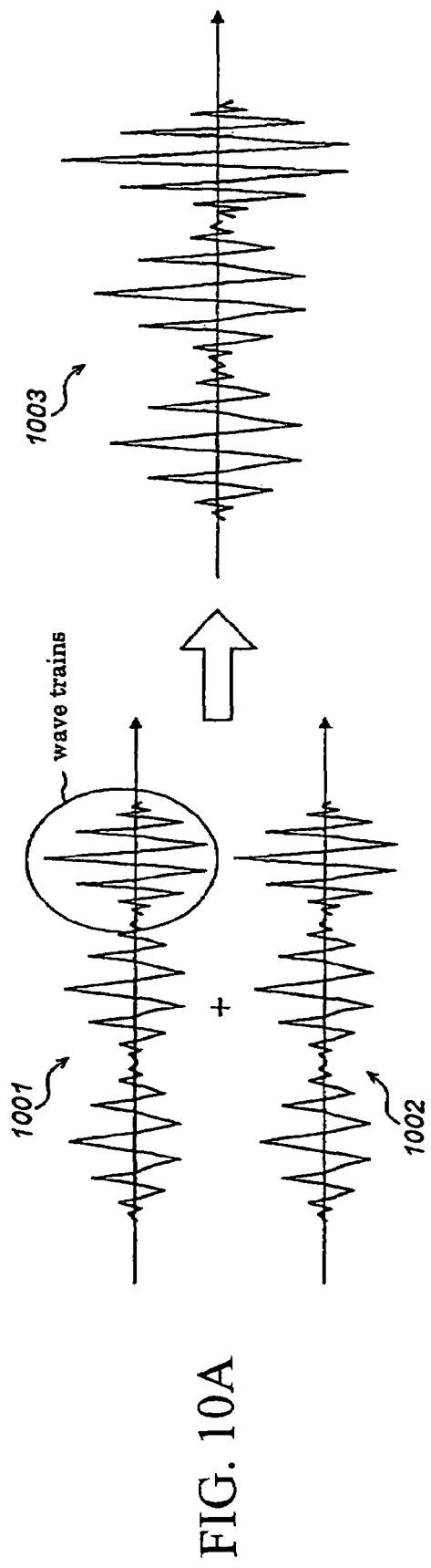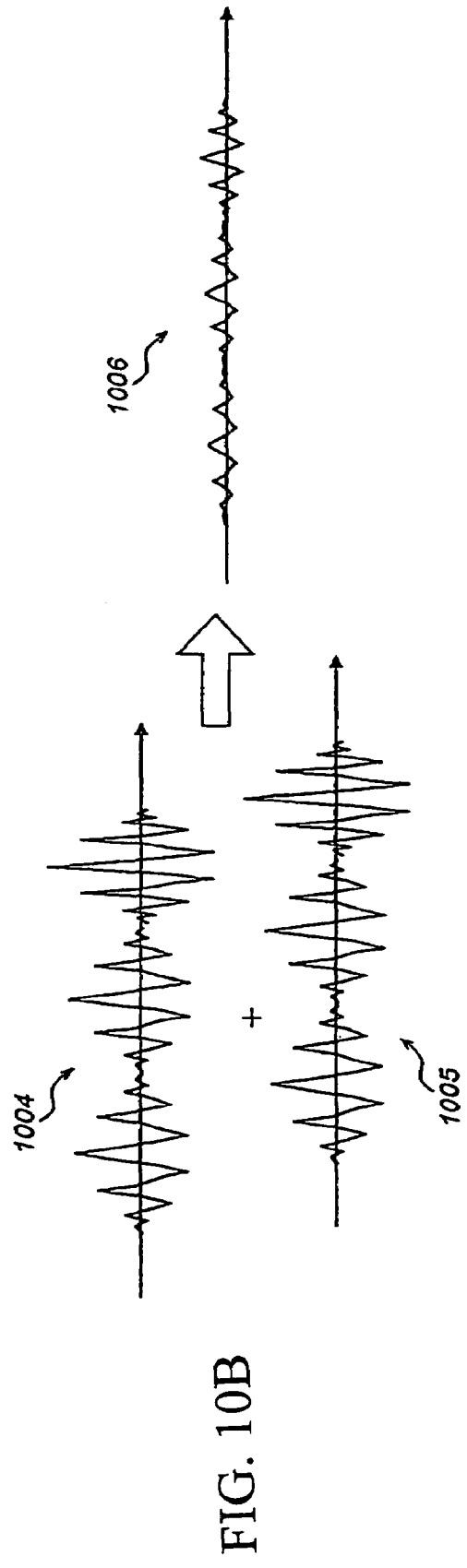
FIG. 10A
FIG. 10B

IMAGE DIAGNOSTIC SYSTEM AND APPARATUS, AND PROCESSING METHOD THEREFOR

TECHNICAL FIELD

This invention generally relates to an image diagnostic system and apparatus, and a processing method therefor.

BACKGROUND OF THE INVENTION

Image diagnostic systems have been used for diagnosing arteriosclerosis, for preoperative diagnosis upon coronary intervention by a high-performance catheter such as a dilatation catheter (i.e., balloon catheter) or stent, and for assessing postoperative results.

Examples of these image diagnostic systems include intravascular ultrasound (IVUS) imaging systems. In general, the intravascular ultrasound imaging system is constructed to control an ultrasonic transducer to perform radial scanning within a blood vessel, to receive a reflected wave(s) (ultrasound echoes) reflected by biotissue (e.g. the blood vessel wall) by the same ultrasonic transducer, to subject the reflected waves to processing such as amplification and detection, and then to construct and display a tomographic image of the blood vessel on the basis of the intensities of the received ultrasound echoes. An example of such a system is described in JP-A-H06-343637.

In addition to these intravascular ultrasound imaging systems, optical coherence tomography (OCT) imaging systems have been developed in recent years for use as image diagnostic systems. In an OCT imaging system, a catheter with an optical fiber incorporated therein is inserted into a blood vessel. The distal end of the optical fiber is provided with an optical lens and an optical mirror. Light is emitted in the blood vessel while radially scanning the optical mirror arranged on the side of the distal end of the optical fiber, and based on light reflected from biotissue forming the blood vessel, a tomographic image of the blood vessel is then constructed and displayed. An example of this system is described in JP-A-2001-79007.

Improved OCT imaging systems have been proposed in recent years which make use of a wavelength swept light source.

As mentioned above, there are a variety of different image diagnostic systems which use different detection principles. Nonetheless, they are all generally characterized in that a tomographic image (i.e. cross-sectional image) is constructed and displayed by performing radial scanning with a probe. For the construction and display of a high-accuracy tomographic image, it is desirable that a transmission/reception cycle of signals from the probe and a rotation cycle for the radical scanning are in complete synchronization. In general, the rotational speed of a radial scan motor is controlled in synchronization with the transmission/reception repeated at a constant clock in the probe.

The rotational speed of a radial scan motor, however, fluctuates due to variations in torque which occur as a result of changes in the degree of bending of a catheter. Therefore, it is difficult to achieve complete synchronization between the rotational speed of the radial scan motor and the cycle of transmission/reception of signals at the probe.

When a tomographic image is constructed with 1,024 lines by controlling the rotational speed of a radial scan motor, for example at 1,800 rpm (30 Hz), the transmissions/receptions can be performed in accordance with a clock speed of 30.72 kHz. If the rotational speed of the radial scan motor fluctuates by 0.05%, however the number of transmissions/receptions increases or decreases by one transmission/reception in every rotation for radial scanning.

When the number of transmissions/receptions increases or decreases by one transmission/reception in every rotation for radial scanning, the resulting displayed tomographic image is blurred in a circumferential direction or is displayed while slowly turning.

SUMMARY

According to one disclosed aspect, an image diagnostic system comprises a probe positionable in a body cavity and configured to repeatedly transmit signals and acquire signals reflected from biotissue surrounding the body cavity, a control unit connected to the probe to produce digital data based on the acquired signals and to construct a tomographic image of the body cavity and the biotissue surrounding the body cavity on the basis of the digital data, and a display unit configured to display the tomographic image. The control means comprises a generation unit configured to output synchronization signals in synchronization with a timing of acquisition cycles of the acquired signals, with the synchronization signals having a higher frequency than output signals outputted corresponding to rotational angles of the probe upon performing the radial scanning. The control unit also comprises a selection unit connected to the generation unit to receive the synchronization signals from the generation unit and the output signals, wherein the selection unit selects and outputs one of the synchronization signals which is first received subsequent to reception of one of the output signals, and a conversion unit configured to convert the reflected signals into digital data and output the digital data responsive to successive inputs of the synchronization signals selected by the selection unit for use in constructing a tomographic image.

Other aspects of the disclosed subject matter involve a method for processing information in an image diagnostic system, an image diagnostic apparatus, a recording medium with a control program stored therein for performing by a computer the information processing method, and a control program.

A tomographic image of good quality can be constructed even when synchronization is not achieved between the rotation cycle of the probe in radial scanning and the cycle of acquisition of as much as one frame of signals in line units from the probe in the image diagnostic system.

BRIEF DESCRIPTION OF THE DRAWING FIGURES

The foregoing and additional aspects of the disclosed system and method will become more apparent from the following detailed description considered with reference to the accompanying drawing figures briefly described below.

FIGS. 7A and 7B are perspective views in cross-section of a blood vessel and the catheter section inserted therein, illustrating movements of the catheter section during an intravascular ultrasound diagnosis.

FIGS. 10A and 10B are waveform diagrams illustrating the principle of a measurement by an OCT imaging system according to a second embodiment of the present invention.

DETAILED DESCRIPTION OF PREFERRED EMBODIMENTS

First Embodiment

1. General Overall Construction of IVUS Imaging System

Figure 1:
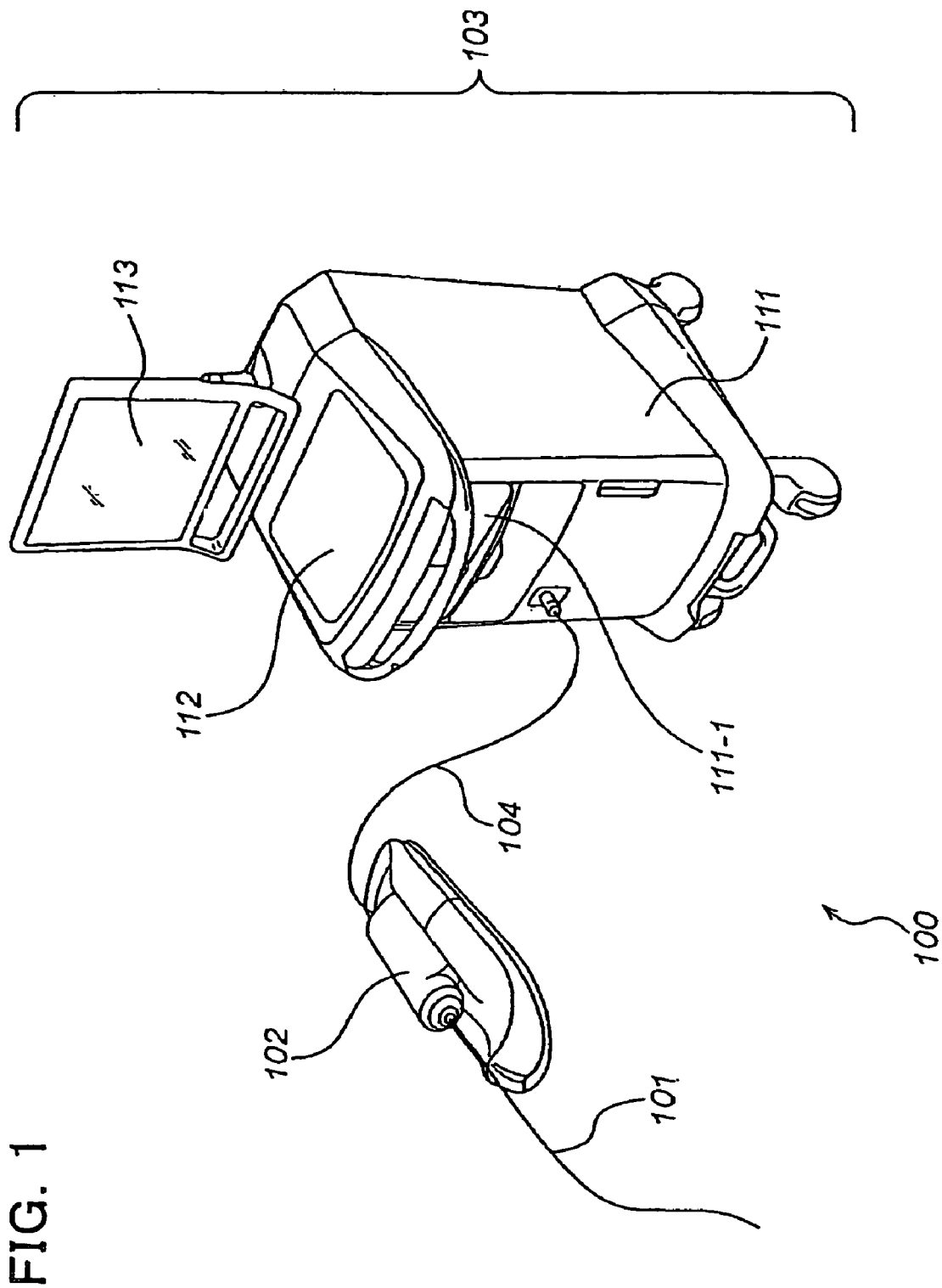
FIG. 1 is a perspective view generally illustrating aspects and features of an IVUS imaging system according to a first embodiment disclosed herein.

Referring to FIG. 1, an intravascular ultrasound (IVUS) imaging system (i.e., image diagnostic system) 100 according to one illustrated and disclosed embodiment includes a catheter section (i.e., probe) 101, a scanner & pull-back unit 102 and an operation control system 103. The scanner & pull-back unit 102 and the operation control system 103 are connected together via a signal line 104 and compose an image diagnostic apparatus.

Figure 4:
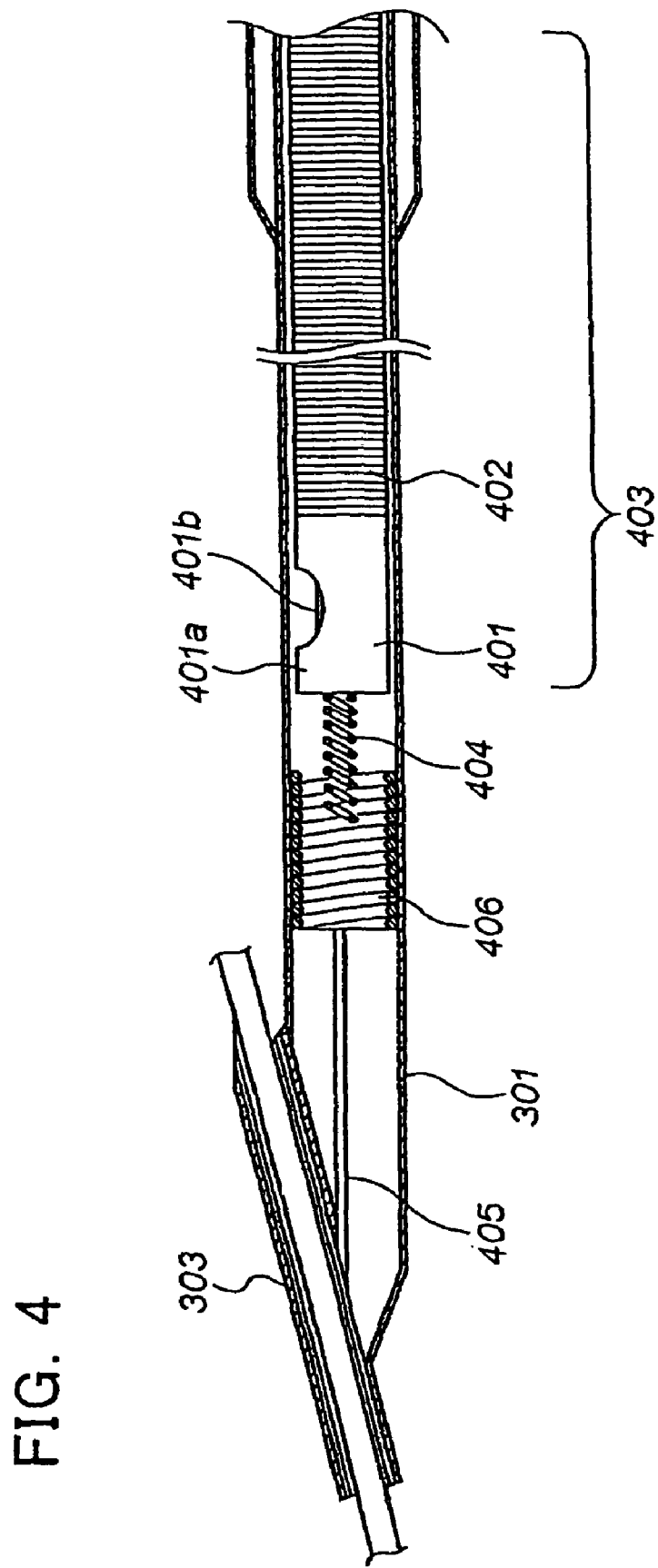
FIG. 4 is a cross-sectional view of the distal end portion of the catheter section shown in FIG. 3.

The catheter section 101 is adapted to be inserted directly into a blood vessel to measure internal conditions of the blood vessel by way of an ultrasonic transducer 401b which is shown in FIG. 4. The scanner & pull-back unit 102 controls movements of the ultrasonic transducer 401b within the catheter section 101.

The operation control system 103 operates to input various preset values upon performing an intravascular ultrasound diagnosis and to also process data acquired by a measurement and to display them as a tomographic image.

The operation control system 103 includes a main control unit 111 which performs processing of data acquired by a measurement and outputs the results of the processing, and a printer/DVD recorder 111-1 which prints the results of the processing in the main control unit 111 or records (i.e., stores) them as data.

The operation control system 103 also includes a control panel 112. Through the control panel 112, a user is able to input various values such as preset values. In addition, the operation control system 103 also includes an LCD monitor (i.e., display) 113, which displays the results of the processing in the main control unit 111.

2. Aspects and Features of IVUS Imaging System

Figure 2:
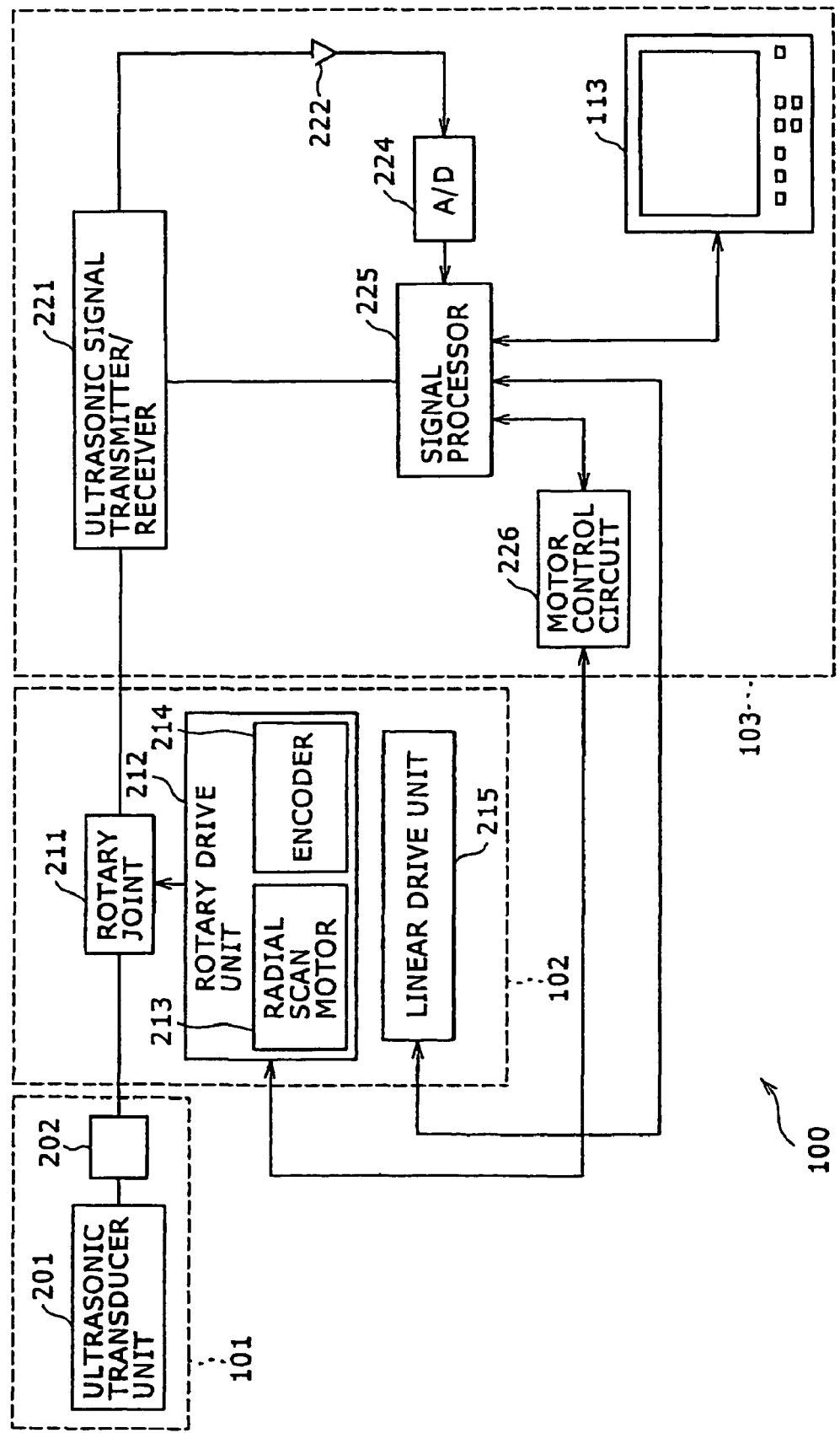
FIG. 2 is a block diagram schematically illustrating additional aspects and features of the IVUS imaging system.

FIG. 2 schematically illustrates in more detail aspects and features of the IVUS imaging system 100 illustrated in FIG. 1. The distal end of the catheter section 101 is internally provided with an ultrasonic transducer unit 201. With the distal end of the catheter section 101 inserted within a blood vessel, the ultrasonic transducer unit 201, responsive to a pulse wave transmitted by an ultrasonic signal transmitter/receiver 221, transmits ultrasound in the direction of a section of the blood vessel, and receives its reflected signals (echoes) and transmits them as signals based on ultrasonic echoes to the ultrasonic signal transmitter/receiver 221 via a connector 202 and a rotary joint 211.

The scanner & pull-back unit 102 includes the rotary joint 211, a rotary drive unit 212 and a linear drive unit 215. The ultrasonic transducer unit 201 within the catheter section 101 is rotatably mounted by the rotary joint 211, which connects a non-rotatable block and a rotatable block with each other, and is rotationally driven by a radial scan motor 213. Rotation of the ultrasonic transducer unit 201 in a circumferential direction within the blood vessel makes it possible to detect ultrasound echo signals required for the construction of a tomographic image of the blood vessel at the predetermined position within the blood vessel.

It is to be noted that the operation of the radial scan motor 213 is controlled based on a control signal transmitted from a signal processor 225 via a motor control circuit 226. Further, each rotation angle of the radial scan motor is detected by an encoder 214. Each output pulse outputted at the encoder 214 is inputted in the signal processor 225, and is used as a timing for the reading of signals to be displayed. This output pulse is also used upon selection of a synchronization signal at a synchronization signal selector to be described subsequently herein.

The scanner & pull-back unit 102 is provided with the linear drive unit 215 and, based on an instruction from the signal processor 225, specifies movements of the catheter section 101 in the direction of its insertion.

The ultrasonic signal transmitter/receiver 221 is provided with a transmission circuit and a reception circuit (not shown). Based on a control signal transmitted from the signal processor 225, the transmission circuit transmits a pulse wave to the ultrasonic transducer unit 201 in the catheter section 101.

The reception circuit, on the other hand, receives the signals based on the ultrasonic echoes from the ultrasonic transducer unit 201 in the catheter section 101. The thus-received signals are amplified by an amplifier 222.

At an A/D converter 224, the signals outputted from the amplifier 222 are sampled to produce digital data (ultrasound echo data) for one line.

Ultrasound echo data produced in line units at the A/D converter 224 are inputted into the signal processor 225. The signal processor 225 converts the ultrasound echo data into video signals to construct tomographic images of the blood vessel at respective positions within the blood vessel, and outputs them at a predetermined frame rate to the LCD monitor 113.

Figure 3:
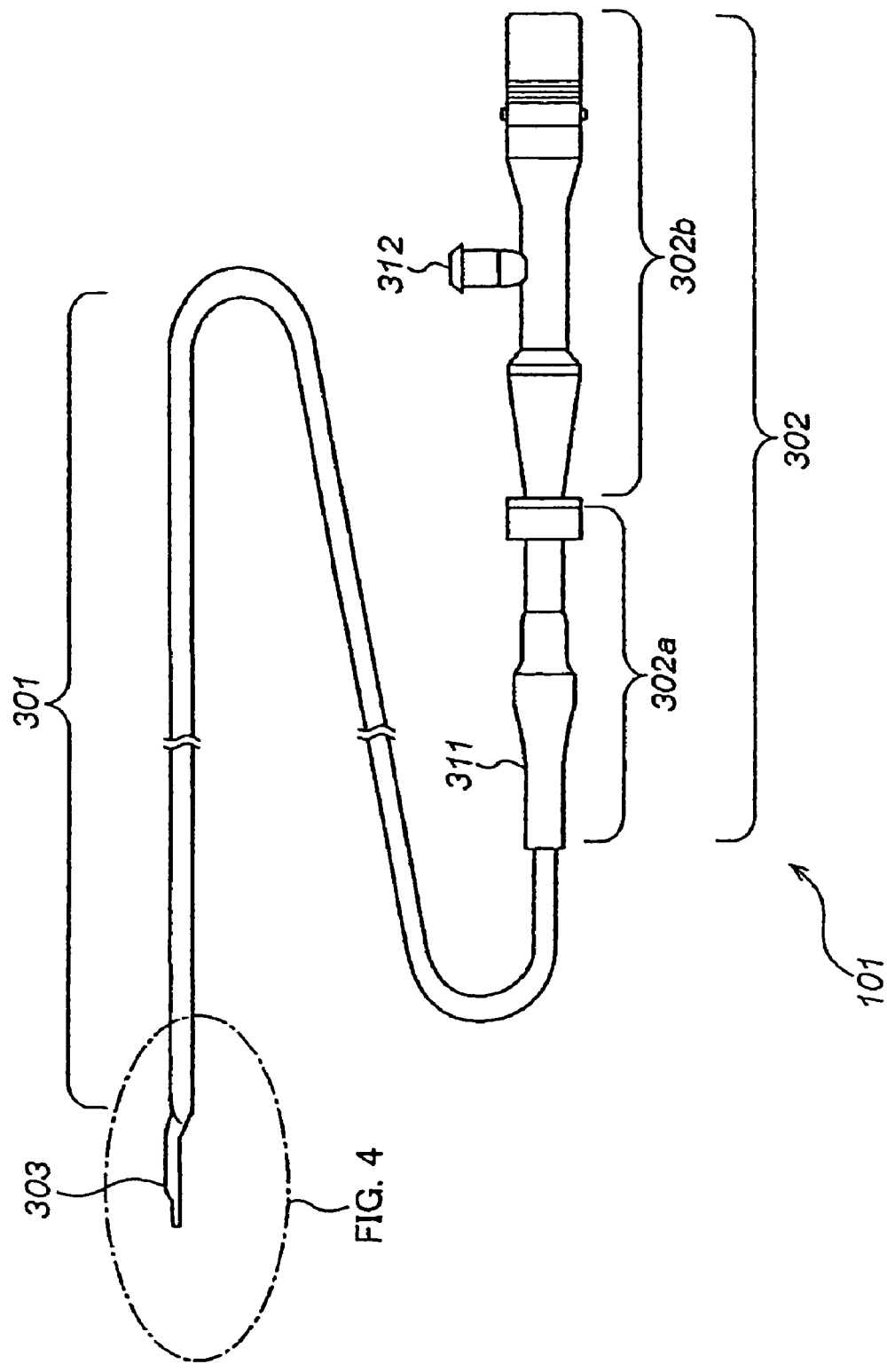
FIG. 3 is a perspective view of the overall construction of a catheter section in the IVUS imaging system.

3. Construction of Catheter Section 3.1 Overall Construction of Catheter Section The overall general construction of the catheter section 101 is illustrated in FIG. 3. The catheter section 101 is constructed as an elongated catheter sheath 301 adapted to be inserted into a blood vessel and a connector 302, not intended to be inserted into the blood vessel, that is arranged on the side of the user's hand to permit handling and operation by the user. A guidewire lumen 303 is provided at the distal end of the catheter sheath. Within the catheter sheath 301 is a lumen which continuously extends from a connecting portion with the guidewire lumen 303 to a connecting portion with the connector 302.

The connector 302 is composed of a sheath connector 302a and a driveshaft connector 302b. The sheath connector 302a is constructed integrally with a proximal end of the catheter sheath 301. The driveshaft connector 302b is arranged on a proximal end of a driveshaft, which will be described subsequently herein, to rotatably hold the driveshaft.

An anti-kink protector 311 is arranged at the boundary portion between the sheath connector 302a and the catheter sheath 301. The arrangement of this anti-kink protector 311 makes it possible to maintain a predetermined degree of stiffness, thereby helping to prevent any short tight twist or curl which might otherwise be caused by a sudden change in torque. The driveshaft connector 302b is provided with an injection port 312 to which a syringe (not illustrated) or the like can be attached to fill up the lumen of the catheter sheath 301 in its entirety with an ultrasound transmission fluid. The proximal end of the driveshaft connector 302b is constructed to be connected to the scanner & pull-back unit 102.

3.2 Construction of Distal End Portion of Catheter Section

FIG. 4 illustrates in more detail the distal end portion of the catheter section 101. Through the lumen of the catheter sheath 301, an imaging core 403 extends over substantially the entire length of the catheter sheath 301. The imaging core 403 is provided with an ultrasonic transducer unit 401 for transmitting and receiving ultrasound and also with the driveshaft 402 for transmitting drive force to rotate the ultrasonic transducer unit 401. The ultrasonic transducer unit 401 is comprised of an ultrasonic transducer 401b and a housing 401a in which the ultrasonic transducer 401b is held. Ultrasound is transmitted from the ultrasonic transducer 401b toward a surrounding biotissue of a body cavity, and reflected ultrasound from the surrounding biotissue of the body cavity is received at the ultrasonic transducer 401b.

The driveshaft 402 is constructed in the form of a coil, accommodates a signal line therein, and extends from the ultrasonic transducer 401b to the connector 302.

The ultrasonic transducer 401b possesses a rectangular or circular shape, and is formed by depositing electrodes on opposite sides of a piezoelectric member made of PZT or the like. The ultrasonic transducer 401b is arranged to assume a position around a central axis of rotation to prevent the driveshaft 402 from causing rotational fluctuations.

The housing 401a is in the form of a short cylindrical tube provided at a part thereof with a cut-off portion. Examples of materials forming the housing 401a include metal or hard resin. Examples of methods of forming include machining such as cutting, laser machining or pressing may be applied to a tubular material to form the cut-off portion, or the desired shape may be directly obtained by injection molding, MIM (metal injection molding) or the like. The housing 401a carries the ultrasonic transducer 401b therein. The proximal end side of the housing 401a is connected with the driveshaft 402. On the distal end side of the housing 401a, a resilient member 404 in the form of a short coil is arranged.

The resilient member 404 is a coil-shaped wire which can be produced by forming a stainless steel wire into a coiled shape. The arrangement of the resilient member 404 on the distal end side of the housing 401a provides the imaging core 403 with improved stability upon rotation. Gold plating can be applied to a surface of the resilient member 404 or housing 401a. As gold is a metal having high x-ray opacity, the gold plating can permit visualization of the resilient member 404 or the housing 401a in an image taken by an x-ray imaging system when the catheter sheath 301 is inserted into a body cavity. As a result, the user can easily ascertain the position of the ultrasonic transducer 401b.

A discharge channel 405 is arranged at a boundary portion between the distal end portion of the catheter sheath 301 and the guidewire lumen 303. The discharge channel 405 is arranged to discharge the ultrasound transmission fluid injected in the priming work.

A reinforcement coil 406 is arranged to avoid kinking of the distal end portion of the catheter sheath 301.

The guidewire lumen 303 has a bore into which the guidewire is adapted to be inserted. The guidewire is inserted beforehand in a body cavity, and is utilized to guide the catheter sheath 301 to a diseased part.

The driveshaft 402 is constructed of a multiple or multilayer, tight coil or the like having properties such that it can rotate and slide relative to the catheter sheath 301. The driveshaft 402 is flexible and can smoothly transmit rotation. The multiple or multilayer, tight coil or the like may be made, for example, of a wire of a metal such as stainless steel.

Owing to the rotation of the driveshaft 402, the lumen can be observed over 360 degrees. To perform an observation over a still greater range, it is only necessary to slide the driveshaft 402 in an axial direction.

Figure 5:
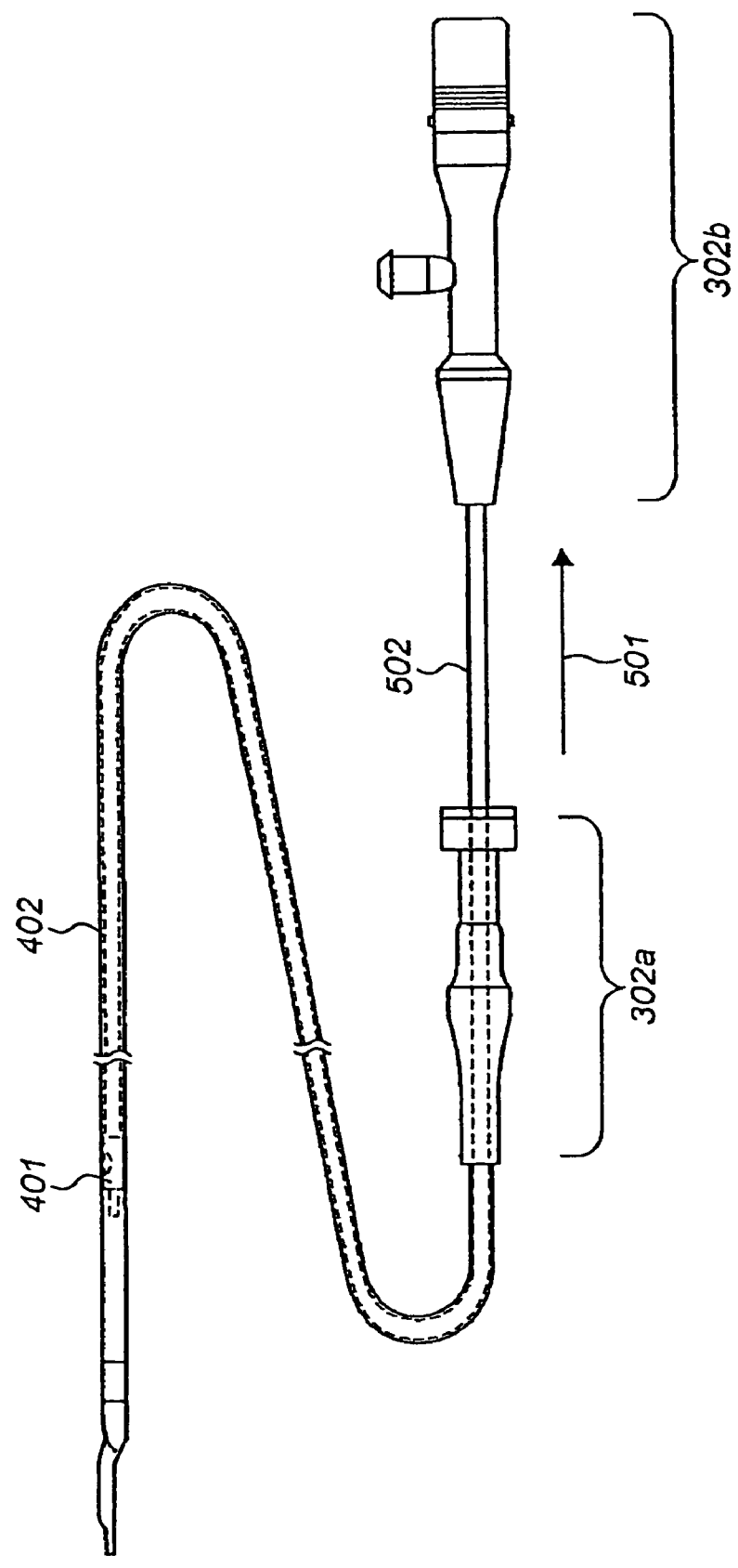
FIG. 5 is a perspective view of the catheter section showing the manner of sliding a driveshaft relative to a catheter sheath in the catheter section.

FIG. 5 schematically illustrates the manner in which the driveshaft 402 is slidably pulled back relative to the catheter sheath 301. As shown in the figure, sliding of the driveshaft connector 302b toward its proximal end (in the direction of arrow 501) with the sheath connector 302a held fixed causes the driveshaft 402, which is accommodated within the driveshaft connector 302b, and the ultrasonic transducer unit 401, which is fixedly secured on the distal end of the driveshaft 402, to slide in the axial direction. This axial sliding may be effected either manually by the user or by an electrical drive. On the distal end side of the driveshaft connector 302b, a protecting inner tube 502 is arranged to avoid exposure of the driveshaft 402 which rotates at a high speed.

4. Features of Signal Processor

Figure 6:
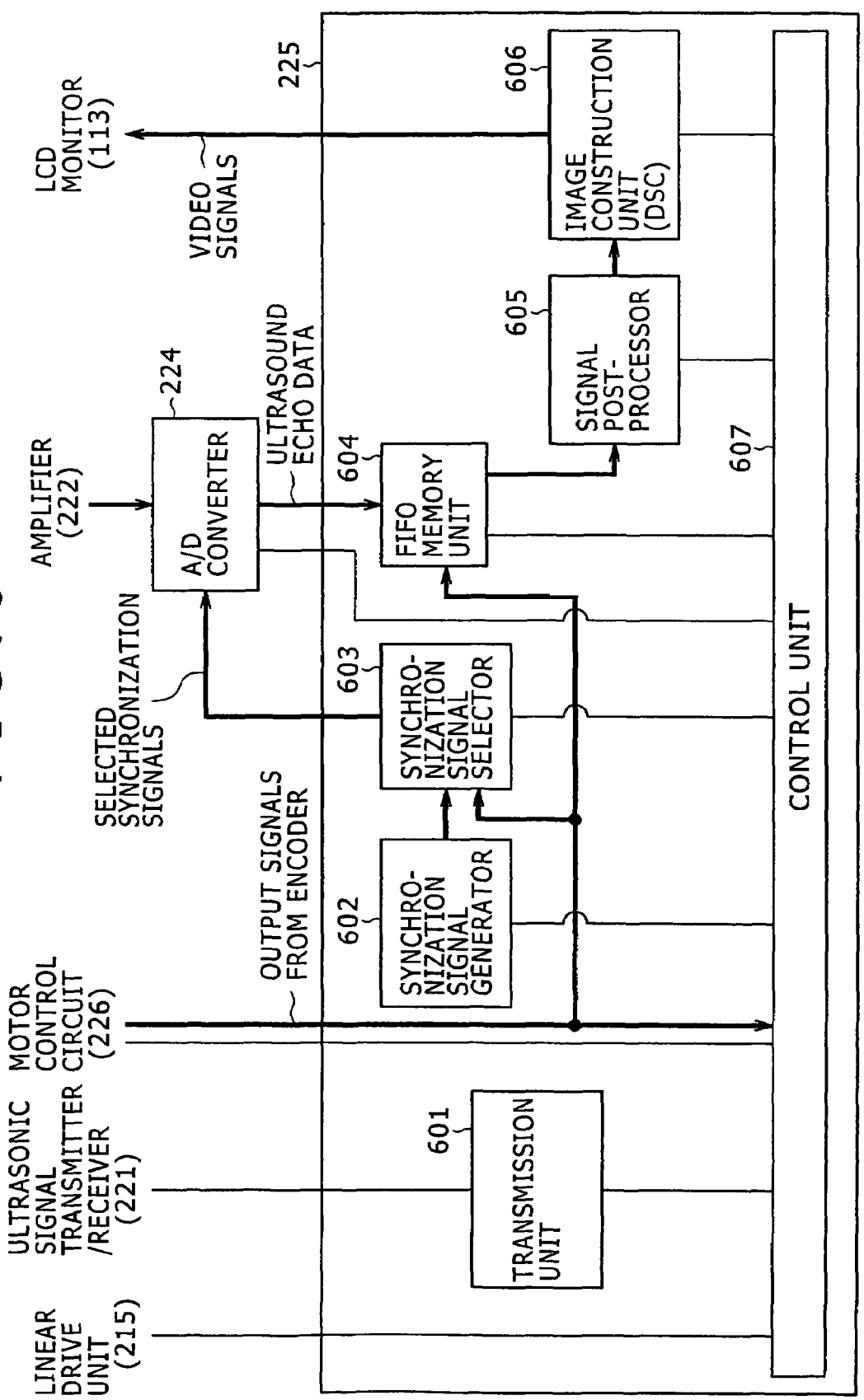
FIG. 6 is a block diagram schematically illustrating aspects of a signal processing unit in the IVUS imaging system.

Various aspects of the signal processor 225 forming a part of the operation control system 103 of the IVUS imaging system 100 are shown in FIG. 6. The signal processor 225 includes a control unit 607 which systematically controls the IVUS imaging system 100 in its entirety, and a transmission unit 601 which transmits operating instructions to the ultrasonic signal transmitter/receiver 221. In this embodiment, the transmission/reception cycle of ultrasonic signals at the ultrasonic signal transmitter/receiver 221 and the rotational speed of the radial scan motor 213 are set to make predetermined sets of the transmission/reception cycle of ultrasonic signals for generating a single frame of an image shorter than predetermined sets of the output cycle of output signals from the encoder 214 for generating a single frame of an image. The following is a brief description of the transmission/reception cycle of ultrasonic signals being shorter than the output cycle of output signals.

The signal processor 225 includes a synchronization signal generator (i.e., a generation unit) 602. This synchronization signal generator 602 generates a synchronization signal which is in synchronization with an operating instruction transmitted from the transmission unit 601, and outputs the synchronization signal to a synchronization signal selector (i.e., a selection unit) 603.

The synchronization signal selector 603 receives output pulses from the encoder 214 and synchronization signals outputted from the synchronization signal generator 602. Among the synchronization signals received, only the synchronization signals first received after the rise of the respective output pulses at the encoder 214 are selected, and the thus-selected synchronization signals are outputted to the A/D converter 224.

More specifically, the synchronization signal selector 603 operates such that when plural synchronization signals have been received from the synchronization signal generator 602 after the rise of each output pulse at the encoder 214 until the rise of the subsequent output pulse at the encoder 214, only the first synchronization signal is selected, and the remaining synchronization signal or signals are thinned out.

From the synchronization signal selector 603, as many synchronization signals are outputted as output pulses from the encoder 214. The synchronization signal selector 603 is designed to monitor the rise of each output pulse at the encoder 214. This embodiment is, however, not specifically limited to the monitoring of the rise of each output pulse. The synchronization signal selector 603 may be designed, for example, to monitor the fall of each output pulse. As a matter of fact, the synchronization signal selector 603 may be designed in any construction insofar as it outputs only one pulse as a synchronization signal during one cycle of output pulses from the encoder 214.

Each synchronization signal outputted from the synchronization signal selector 603 is inputted to the A/D converter 224. At the A/D converter 224, the synchronization signal inputted from the synchronization signal selector 603 is used as a trigger to produce one line of digital data from the corresponding ultrasound echo signals.

Each line unit of ultrasound echo data produced at the A/D converter 224 is outputted to a FIFO memory unit 604. The FIFO memory unit 604 once stores each line unit of ultrasound echo data inputted from the A/D converter 224. In synchronization with an output pulse from the encoder 214, the line unit of ultrasound echo data is read and outputted to a signal post-processor 605.

The signal post-processor 605 performs processing such as logarithmic conversion, frame correlation, gamma correction, contrast adjustment and sharpness filtering on the ultrasound echo data transmitted from the FIFO memory unit 604, and outputs the resulting data to an image construction unit 606.

At the image construction unit 606, streams of ultrasound echo data in the transmission/reception units (line units) of ultrasound are converted into video signals. Based on the video signals, tomographic images to be displayed on the LCD monitor 113 are constructed.

5. Operation of the Catheter Part 101 Upon Intravascular Ultrasound Diagnosis

FIGS. 7A and 7B schematically illustrate movements of the catheter section 101 during an intravascular ultrasound (IVUS) diagnosis. FIGS. 7A and 7B illustrate, in cross-section and perspective view respectively, a blood vessel with the catheter section 101 inserted therein.

FIG. 7A illustrates a section of the blood vessel 701 in which the catheter section 101 is inserted. As described above, the ultrasonic transducer 401b is internally mounted at the distal end of the catheter section 101, and is rotated in the direction of arrow 702 by the radial scan motor 213.

From the ultrasonic transducer 401b, the transmission/reception of ultrasound is performed at respective rotation angles. Lines 1, 2, ..., 1024 indicate the transmitting directions of ultrasound at the respective rotation angles. In this embodiment, 1,024 transmissions/receptions are intermittently performed while the ultrasonic transducer 401b rotates over 360 degrees in a predetermined blood vessel section (701). The number of transmissions/receptions of ultrasound during a 360-degree rotation is not limited specifically to 1,024, but can be set as desired. The scanning that is repeated with the transmission/reception of a signal while rotating the ultrasonic transducer 401b as described above is generally called "radial scan" or "radial scanning".

Such transmissions/receptions of ultrasound are performed while advancing the catheter section 101 through the blood vessel in the direction of arrow 703 shown in FIG. 7B.

6. Processing at the A/D Converter 224 and Signal Processor 225

Figure 8:
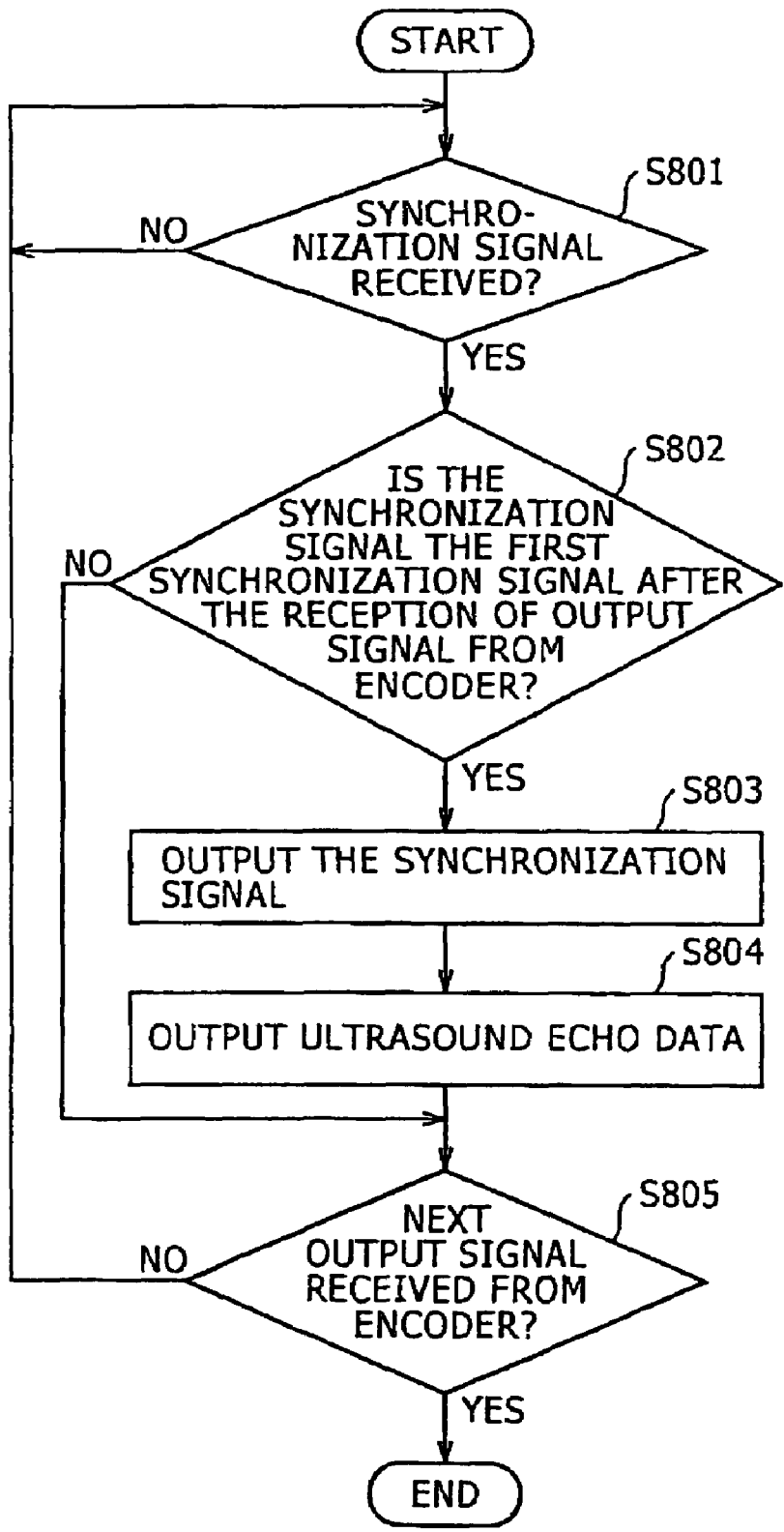
FIG. 8 is a flow chart illustrating operational aspects associated with processing at an A/D converter and signal processor during the intravascular ultrasound diagnosis.

The processing at the A/D converter 224 and signal processor 225 during an intravascular ultrasound diagnosis by the IVUS imaging system 100 is described below with reference top FIG. 8. Whenever the synchronization signal selector 603 receives an output pulse from the encoder 214, the processing shown in FIG. 8 is started.

In step S801, a determination is made as to whether or not the synchronization signal selector 603 has received a synchronization signal from the synchronization signal generator 602. If no synchronization signal has been received, the process waits until a synchronization signal is received. Once a synchronization signal is received, the process advances to step S802.

In step S802, a determination is made as to whether or not the synchronization signal received in step S801 is the first synchronization signal after the output pulse received from the encoder 214 upon starting the processing.

If the synchronization signal is determined to be the first synchronization signal in step S802, the process advances to step S803 in which the synchronization signal so received is outputted to the A/D converter 224. The process then advances to step S804.

In step S804, the A/D converter 224 uses the synchronization signal as a trigger to produce ultrasound echo data, and outputs the ultrasound echo data to the FIFO (first in, first out) memory unit 604.

If the synchronization signal is not determined to be the first synchronization signal in step S802, the process advances to step S805 without outputting the thus-received synchronization signal to the A/D converter 224.

In step S805, the synchronization signal selector 603 determines whether or not the next output pulse has been received from the encoder 214. If the next output pulse has not been received yet, the process returns to step S801. If the next output pulse has been received, on the other hand, the current processing is ended.

7. Specific Example of the Processing at the A/D Converter 224 and Signal Processor A specific example of the processing at the A/D converter 224 and signal processor 225 is set forth below with reference to FIG. 9 illustrating a timing chart when output pulses from the encoder 214 and a transmission/reception timing of the ultrasonic transducer are out of synchronization.

Figure 9:
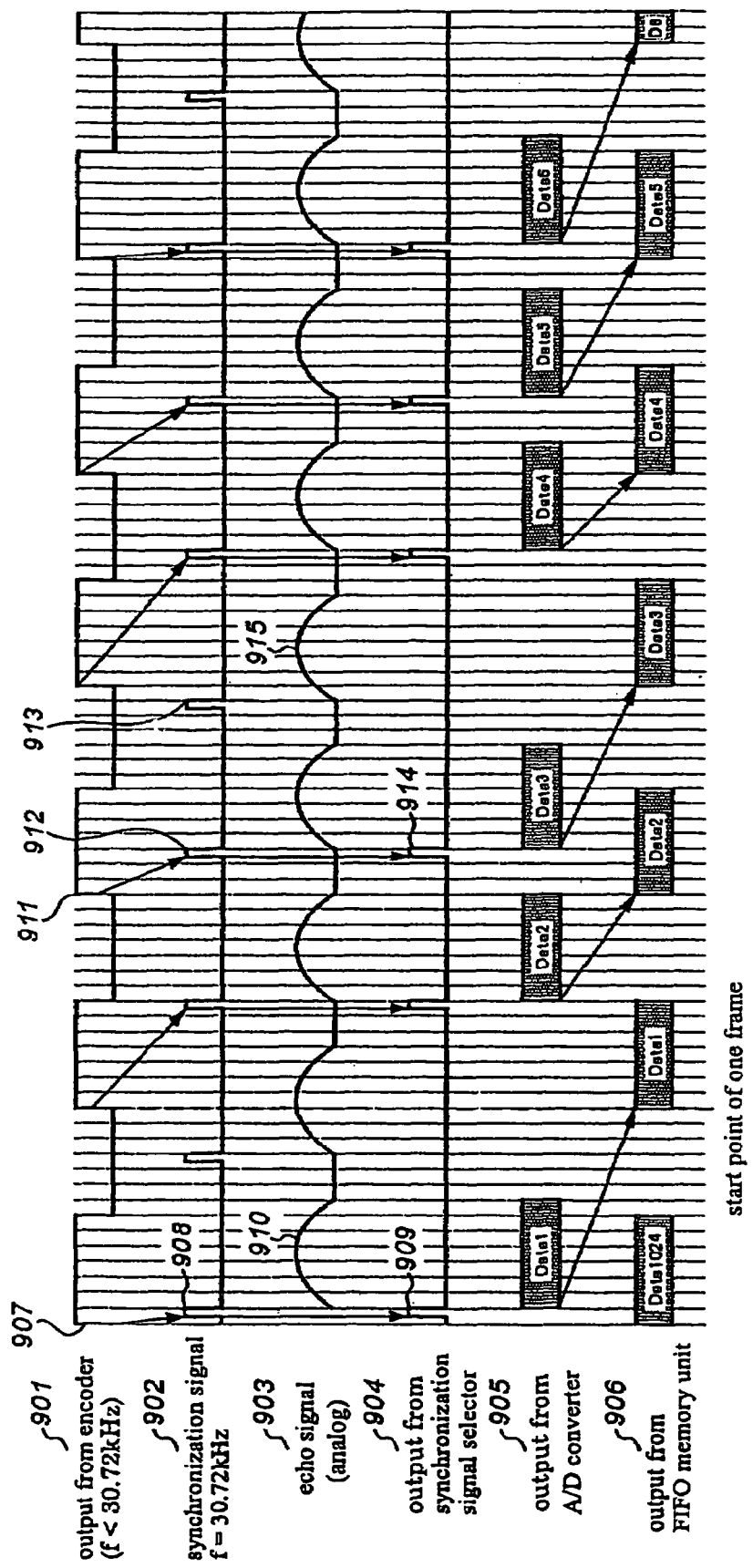
FIG. 9 is a timing chart illustrating when output pulses from an encoder and a transmission/reception timing of an ultrasonic transducer are in synchronization.

FIG. 9 illustrates a timing 901 of output pulses from the encoder 214, a timing 902 of synchronization signals produced at the synchronization signal generator 602, a timing 903 of ultrasonic echo signals to be inputted to the A/D converter 224, and a timing 904 of synchronization signals to be selectively outputted at the synchronization signal selector 603. In addition, FIG. 9 schematically illustrates ultrasound echo data 905 produced at the A/D converter 224 and a timing 906 of ultrasound echo data to be read from the FIFO memory unit 604.

As illustrated in FIG. 9, upon receipt of a synchronization signal (908) first produced and outputted at the synchronization signal generator 602 after a rise (907) of an output pulse at the encoder 214, the synchronization signal selector 603 outputs the synchronization signal (909) to the A/D converter 224. At the A/D converter 224, the synchronization signal received from the synchronization signal selector 603 is used as a trigger to subject an ultrasound echo signal (910) to A/D conversion to produce ultrasound echo data (Data 1). The ultrasound echo data (Data 1) are then stored in the FIFO memory unit 604. Data 1 stored in the FIFO memory unit 604 are read in synchronization with an output pulse from the encoder 214.

In the IVUS imaging system according to this embodiment, the transmission/reception cycle of ultrasonic signals at the ultrasonic signal transmitter/receiver 221 is set shorter than the output cycle of output pulses from the encoder 214. Subsequent to a rise (911) of an output pulse at the encoder 214, two synchronization signals (912, 913) may, therefore, be outputted from the synchronization signal generator 602 in some instances.

In such a case, the first synchronization signal (912) is selected at the synchronization signal selector 603, and is outputted to the A/D converter 224 (914). On the other hand, the second synchronization signal (913) is not selected at the synchronization signal selector 603, and therefore, is not outputted to the A/D converter 224. As a result, an ultrasound echo signal (915) inputted to the A/D converter 224 subsequent to the reception of the second synchronization signal (913) at the synchronization signal selector 603 is not subjected to A/D conversion and is thinned out.

As is evident from the above description, the IVUS imaging system according to this embodiment makes it possible to produce ultrasound echo data in accordance with the rotation cycle of the probe in radial scanning even when synchronization is not achieved between the rotation cycle of the probe in the radial scanning and the transmission/reception cycle of ultrasound from the probe. In other words, it becomes possible to produce ultrasound echo data after thinning out any extra ultrasonic echo signals inputted beyond the number of output pulses from the encoder.

As a result, it is possible to eliminate an inconvenience such as that associated with other systems in which a tomographic image may be displayed in a blurred manner in the circumferential direction or may be displayed while slowly turning.

Second Embodiment

The description above describes about the processing at the A/D converter and the signal processor in an IVUS imaging system when the rotation cycle for radial scanning by the ultrasonic transducer and the transmission/reception cycle of ultrasonic signals at the probe are out of synchronization. However, the disclosure here is not specifically limited to IVUS imaging systems, but rather has useful application to other image diagnostic systems. The following describes application of the disclosure here to an optical coherence tomography (OCT) imaging system.

1. Measurement Principle of OCT Imaging System

The measurement principle of the OCT imaging system will first be briefly described. Because light is electromagnetic radiation, it generally has the property that beams of light interfere with each other when they are superimposed. The interference property that defines whether light interferes readily or hardly is called "coherence", and in general OCT imaging systems, low-coherence light of low interference property is used.

When time is plotted along the abscissa and the electric field is plotted along the ordinate, low-coherence light becomes random signals as indicated at 1001 and 1002 in FIG. 10A. Individual peaks in the figure are called "wave trains", and have their own, mutually-independent phases and amplitudes. When the same wave trains (1001 and 1002) overlap each other as in FIG. 10A, they interfere with each other to intensify each other (see 1003). On the other hand, when there is a slight delay in time between wave trains (1004 and 1005 in FIG. 10B), they cancel each other so that no interference light is observed as shown at 1006 in FIG. 10B.

Figure 11:
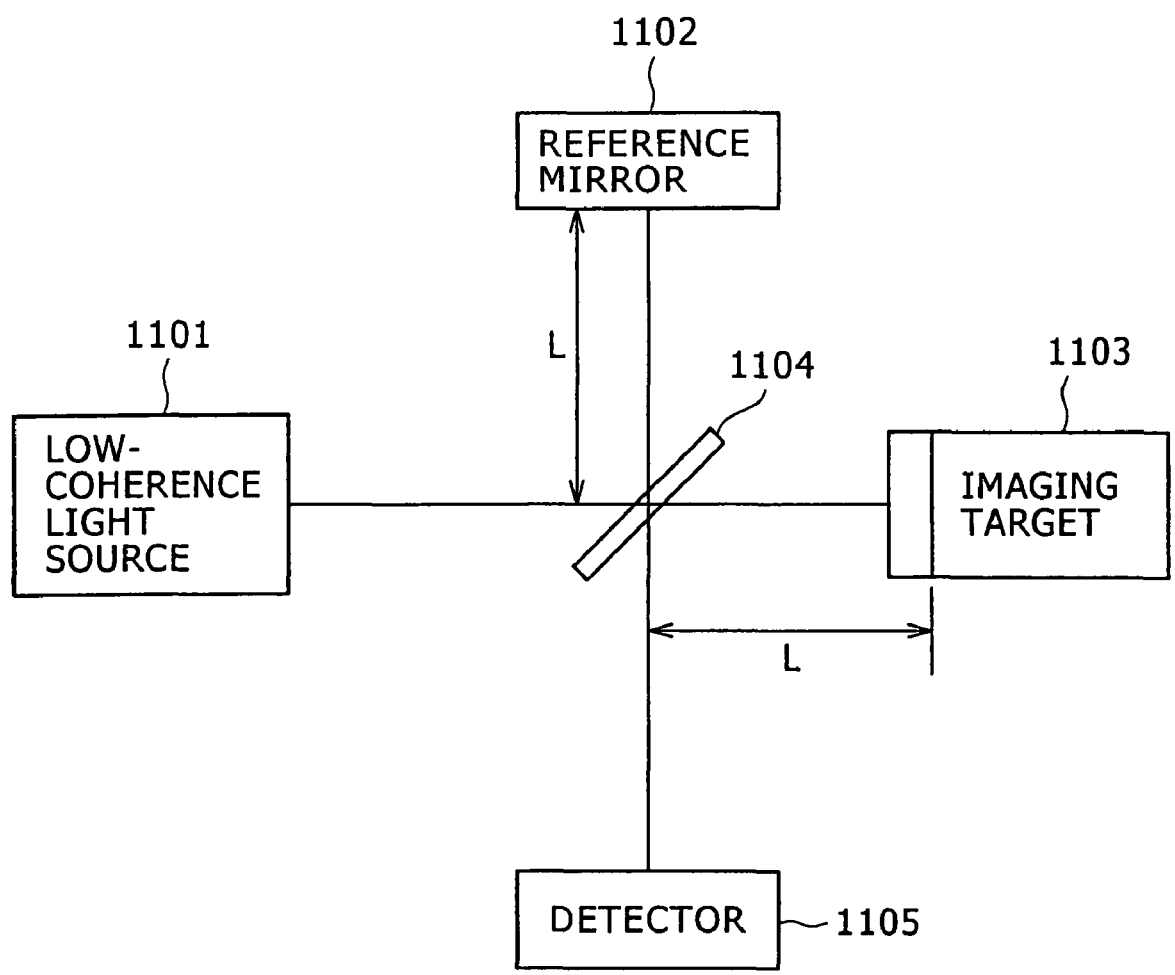
FIG. 11 is a block diagram illustrating the basic principle of the OCT imaging system.

The OCT imaging system makes use of such properties, and the basic principle of the system is illustrated in FIG. 11. As shown in the figure, light emitted from a low-coherence light source 1101 is split at a beam splitter 1104 between a reference optical path and a sample optical path. The resulting light beam in the reference optical path is then directed toward a reference mirror 1102. Further the resulting light beam in the sample optical path is then directed toward an imaging target 1103. At this time, reflected light which is returning from the path of the imaging target includes light reflected on the surface of the imaging target, light reflected at shallow points in the imaging target, and light reflected at deep points in the imaging target.

As the incident light is low-coherence light, the reflected light on which interference can be observed is, however, only the reflected light from a reflection surface located at a position apart by a distance of $L+\Delta L/2$ from the beam splitter 1104, where L represents the distance from the beam splitter 1104 to the reference mirror 1102, and $\Delta L$ represents a coherence length.

By changing the distance from the beam splitter 1104 to the reference mirror 1102, it is possible to selectively detect at a detector 1105 only reflected light from a reflection surface, which corresponds to the thus-changed distance, in the imaging target. A tomographic image can then be constructed by visualizing internal structural information of the imaging target on the basis of the intensities of reflected light beams corresponding to such respective distances.

2. General Overall Construction of OCT Imaging System

The general overall construction of the OCT imaging system is similar to that of the IVUS imaging system described above in the first embodiment (see FIG. 1). A description of the general overall construction is thus not repeated.

3. Aspects and Features of OCT Imaging System

Figure 12:
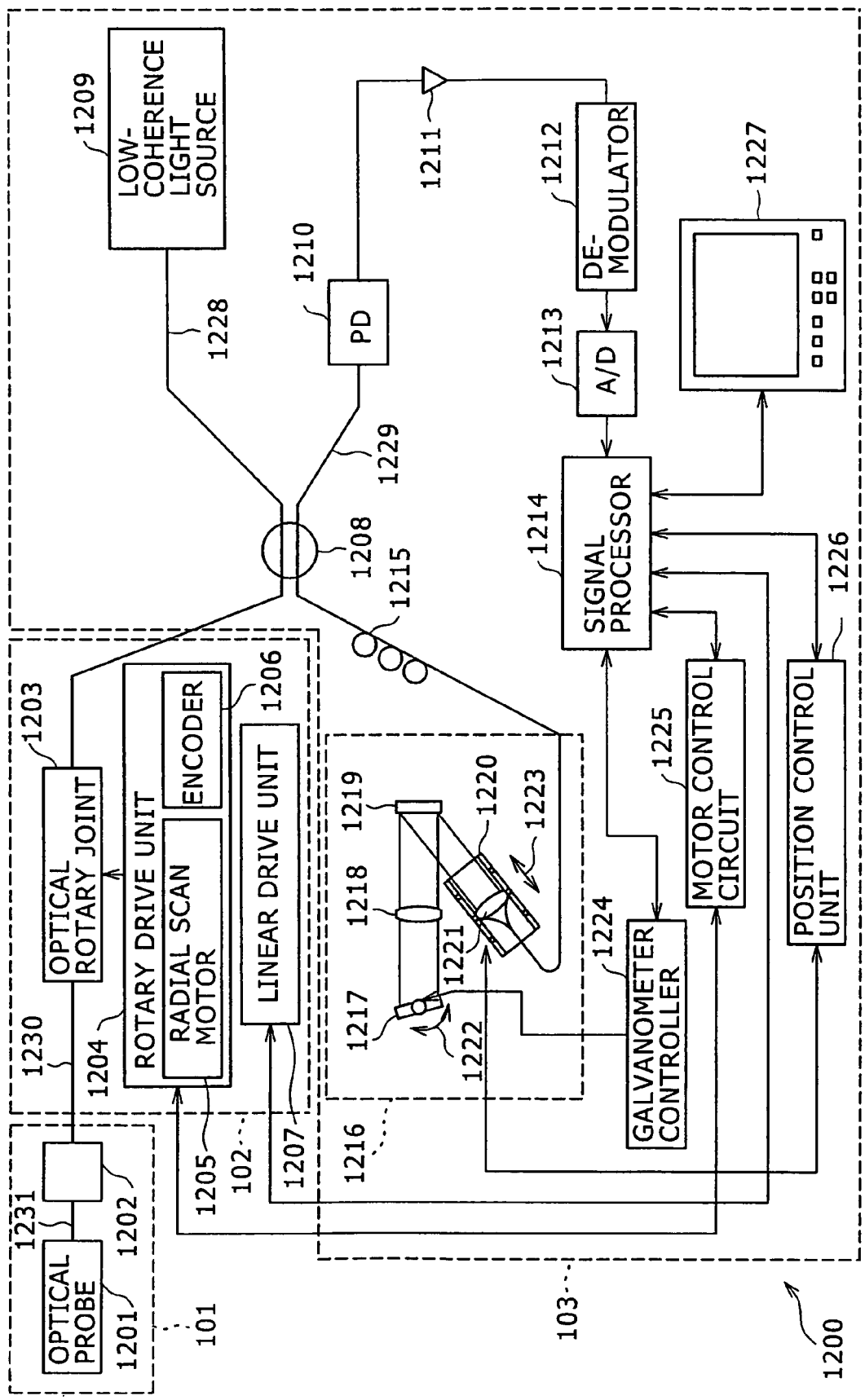
FIG. 12 is a block diagram schematically illustrating aspects of the OCT imaging system.

FIG. 12 illustrates features and aspects associated with the OCT imaging system (image diagnostic system) 1200. The system includes a low-coherence light source 1209 such as an ultra-high intensity, light emitting diode. The low-coherence light source 1209 has a wavelength around 1,310 nm, and outputs low-coherence light showing interference property only in such a short distance range that its coherent length approximately ranges from several micrometers to over ten micrometers.

When the light is split into two and the resulting beams of light are combined back, the combined light is, therefore, detected as coherent light when the difference between the two optical path lengths from the splitting point to the combining point falls within a short distance range around 17 µm, but no coherent light is detected when the difference in optical path length is greater than the above-described range.

The light from the low-coherence light source 1209 enters a proximal end face of a first single mode fiber 1228, and is transmitted toward its distal end face. At an optical coupler 1208 arranged midway along the first single mode fiber 1228, the first single mode fiber 1228 is optically coupled with a second single mode fiber 1229. Therefore, the light transmitted through the first single mode fiber 1228 is split into two by the optical coupler 1208 and the resulting two beams of light are transmitted further.

On the sample optical path side of a more distal end of the first single mode fiber 1228 than the optical coupler 1208, an optical rotary joint 1203 is arranged to connect a non-rotatable block and a rotatable block with each other such that light can be transmitted.

Further, an optical-probe connector 1202 is detachably connected to a distal end of a third single mode fiber 1230 in the optical rotary joint 1203. Via the connector 1202, the light from the low-coherence light source 1209 is transmitted to a fourth single mode fiber 1231, which is inserted in an optical probe 1201 and is rotationally drivable.

The transmitted light is irradiated from a distal end side of the optical probe 1201 toward a surrounding biotissue of a body cavity while performing radial scanning. A portion of reflected light scattered on a surface or interior of the biotissue is collected by the optical probe 1201, and returns to the side of the first single mode fiber 1228 through the reverse optical path. A portion of the thus-collected, reflected light is transferred by the optical coupler 1208 to the side of the second single mode fiber 1229, and is introduced into a photodetector (for example, photodiode 1210) from an end of the second single mode fiber 1229.

It is to be noted that the rotatable block side of the optical rotary joint 1203 is rotationally driven by a radial scan motor 1205 of a rotary drive unit 1204. Further, rotation angles of the radial scan motor 1205 are detected by an encoder 1206, and are outputted as output pulses. The optical rotary joint 1203 is provided with a linear drive unit 1207 that, based on an instruction from a signal processor 1214, controls movement of the catheter section 101 in the direction of its insertion.

On the reference optical path side of a more distal end of the second single mode fiber 1229 than the optical coupler 1208, an optical path length (OPL) varying mechanism 1216 is arranged to vary the optical path length of reference light.

This OPL varying mechanism 1216 is provided with a first OPL varying means for varying the optical path length, which corresponds to the examinable range in the direction of the depth of the biotissue, at high speed and also with a second OPL varying means for varying the optical path length by a length equivalent to a variation in the length of a new optical probe to absorb or adjust the variation when the new optical probe is used as a replacement since the probe used for inserting the blood vessel of human is generally disposable.

Opposing a distal end of the second single mode fiber 1229, a grating (diffraction grating) 1219 is arranged via a collimator lens 1221 which is mounted together with the distal end of the second single mode fiber 1229 on a single axis stage 1220 and is movable in the direction indicated by arrow 1223. Further, a galvanometer mirror 1217 which is rotatable over small angles is mounted as the first OPL varying means via the grating 1219 and an associated lens 1218. This galvanometer mirror 1217 is rotated at high speed in the direction of arrow 1222 by a galvanometer controller 1224.

The galvanometer mirror 1217 serves to reflect light by its mirror, and functions as a reference mirror. The galvanometer mirror 1217 is constructed such that its mirror mounted on a movable part of its galvanometer is rotated at high speed by applying an a.c. drive signal to the galvanometer.

More specifically, by applying a drive signal to the galvanometer from the galvanometer controller 1224 and rotating the galvanometer at high speed in the direction of arrow 1222 with the drive signal, the optical path length of reference light is varied at high speed by an optical path length equivalent to a detection range in the direction of the depth of the biotissue. A single cycle of variations in optical path length becomes a cycle that produces interference light data for a single line (in line unit).

On the other hand, the single axis stage 1120 forms the second OPL varying means having a variable OPL range just enough to absorb a variation in the optical path length of a new optical probe when the optical probe 1201 is replaced by the new optical probe. In addition, the single axis stage 1220 is also equipped with a function as an adjustment means for adjusting an offset. Even when the distal end of the optical probe 1201 is not in close contact with a surface of the biotissue, for example, the optical probe can still be set in such a state as interfering from a position on the surface of the biotissue by slightly varying the optical path length with the single axis stage 1220.

The light varied in optical path length by the OPL varying mechanism 1216 is combined with the light, which has escaped from the side of the first single mode fiber 1228, at the optical coupler 1208 arranged midway along the second single mode fiber 1229, and the combined light is received at the photodiode 1210.

The light received at the photodiode 1210 is amplified by an amplifier 1211, and is then inputted into a demodulator 1212. At the demodulator 1212, demodulation processing is performed to extract only the signal portion of the interfered light, and the output of the demodulator 1212 is inputted into an A/D converter 1213.

At the A/D converter 1213, interference light signals are sampled as much as for 200 points to produce digital data (interference data) for one line. The sampling frequency is a value obtained by dividing with 200 the time required for a single scan of the optical path length.

The interference light data in the line unit, which have been produced at the A/D converter 1213, are inputted into the signal processor 1214. At this signal processor 1214, the interference light data in the direction of the depth are converted into video signals to constitute tomographic images at respective positions in the blood vessel. These tomographic images are then outputted at a predetermined frame rate to an LCD monitor 1227.

The signal processor 1214 is connected with a position control unit 1226. The signal processor 1214 performs control of the position of the single axis stage 1220 via the position control unit 1226. In addition, the signal processor 1214 is also connected with a motor control circuit 1225 to control rotational drive by the radial scan motor 1205.

Further, the signal processor 1214 is also connected with the galvanometer controller 1224 which controls the scanning of the optical path length of the reference mirror (galvanometer mirror). The galvanometer controller 1224 outputs a drive signal (synchronization signal) to the signal processor 1214, and based on this drive signal, the motor control circuit 1225 is synchronized with the galvanometer controller 1224.

This synchronization, however, may be offset due to a variation or the like in torque inside the blood vessel or the like.

4. Construction of Catheter Section

Figure 13:
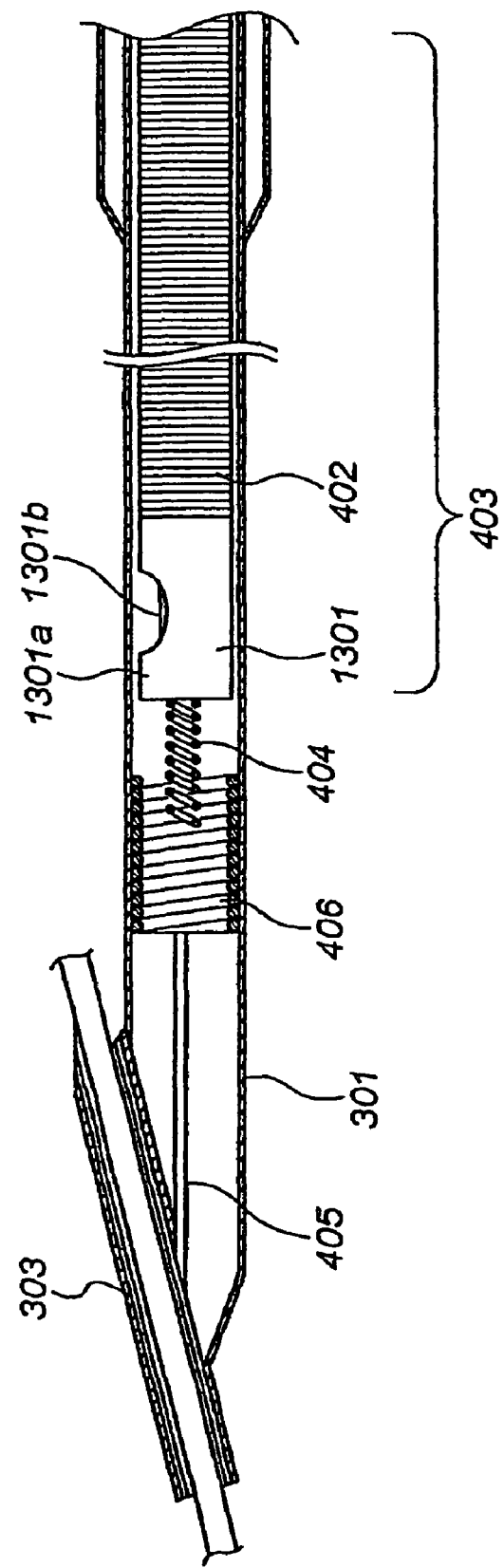
FIG. 13 is a cross-sectional view of a distal end portion of a catheter section in the OCT imaging system.

The overall construction of the catheter section 101 is the same as the construction of the catheter section in the IVUS imaging system described above in the first embodiment, and so such description is not repeated here. Referring to FIG. 13, the following is a description primarily of the differences in the construction of the distal end portion of the catheter section 101.

In FIG. 13, an optical probe 1301 which irradiates/receives low-coherence light is arranged within the lumen of the catheter sheath 301. The optical probe 1301 is provided with a prism or mirror 1301b to perform lateral irradiation. The optical probe 1301 includes the prism or mirror 1301b and a housing 1301a with the prism or mirror 1301b held therein. The optical probe 1301 irradiates low-coherence light toward a surrounding biotissue of a body cavity from the prism or mirror 1301b, and receives reflected light at the prism or mirror 1301b from the surrounding biotissue of the body cavity.

An optical fiber is disposed through the drive shaft 402, and extends from the housing 1301a to the connector 1202. As the advance injection of physiological saline (priming work) is not absolutely needed in the OCT imaging system according to this embodiment, the priming discharge channel 405 formed at the boundary portion between the distal end portion of the catheter sheath 301 and the guidewire lumen 303 may be omitted.

5. Features of the Signal Processor

Figure 14:
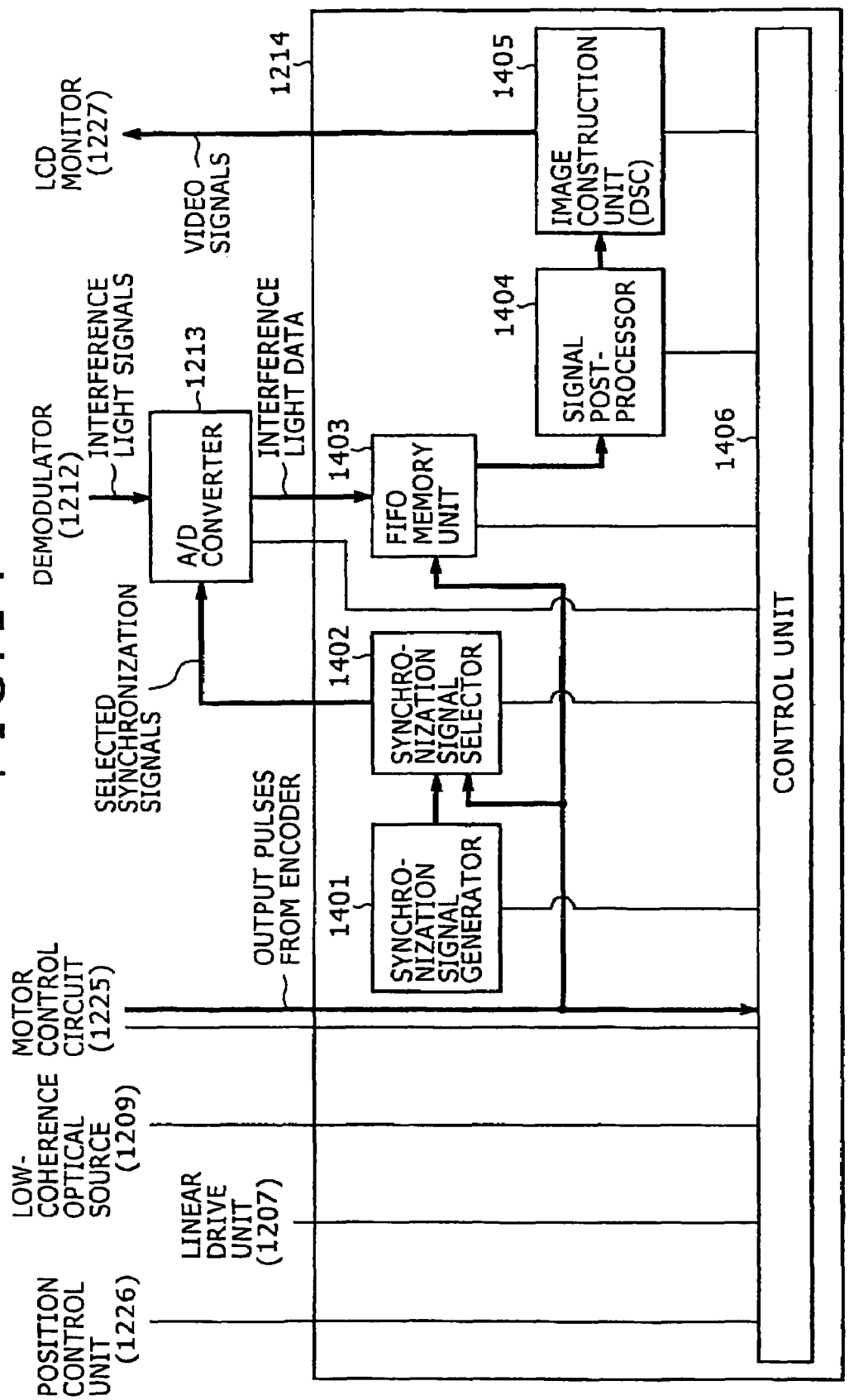
FIG. 14 is a block diagram schematically illustrating aspects of a signal processor in the OCT imaging system.

Features associated with the signal processor 1214 in the OCT imaging system 1200 are illustrated in FIG. 14. The signal processor 1214 includes a main control unit 1406 which systematically controls the OCT imaging system 1200 in its entirety. The signal processor also includes a synchronization signal generator (i.e., generation unit) 1401. This synchronization signal generator 1401 generates a synchronization signal which is in synchronization with the cycle of variations in the optical path length of a reference mirror as obtained from the galvanometer mirror 1224, and outputs the synchronization signal to a synchronization signal selector 1402. Predetermined sets of the cycle of variations in the optical path length of the reference mirror for generating a single frame of an image is set shorter than predetermined sets of the output cycle of output pulses from the encoder 1206 for generating a single frame of an image. The following is a brief description of the cycle of variations in the optical path length being set shorter than the output cycle of output pulses.

A synchronization signal selector (i.e., selection unit) 1402 receives output pulses from the encoder 1206 and synchronization signals outputted from the synchronization signal generator 1401. Among the synchronization signals so received, only the synchronization signals first received after the rise of the respective output pulses at the encoder 1206 are selected, and the thus-selected synchronization signals are outputted to the A/D converter (i.e., conversion unit) 1213.

More specifically, the synchronization signal selector 1402 functions such that, when plural synchronization signals have been received from the synchronization signal generator 1401 after the rise of each output pulse at the encoder 1206 until the rise of the subsequent output pulse at the encoder 1206, only the first synchronization signal is selected and the remaining synchronization signal or signals are thinned out.

From the synchronization signal selector 1402, as many synchronization signals are outputted as output pulses from the encoder 1206. The synchronization signal selector 1402 is designed to monitor the rise of each output pulse at the encoder 1206. This embodiment is, however, not limited specifically to the monitoring of the rise of each output pulse. The synchronization signal selector 1402 may be designed, for example, to monitor the fall of each output pulse. As a matter of fact, the synchronization signal selector 1402 may be designed in any construction insofar as it outputs only one pulse as a synchronization signal during one cycle of output pulses from the encoder 1206.

Each synchronization signal outputted from the synchronization signal selector 1402 is inputted to the A/D converter 1213. At the A/D converter 1213, the synchronization signal inputted from the synchronization signal selector 1402 is used as a trigger to produce one line of digital data (interference light data). The sampling frequency is a value obtained by dividing the time required for a single scan of the optical path length by 200.

Each line unit of interference light data produced at the A/D converter 1213 is inputted to an FIFO memory unit 1403.

The FIFO memory unit 1403 once stores the interference light data inputted from the A/D converter 1213. In synchronization with an output pulse from the encoder 1206, the interference light data are read and outputted to a signal post-processor 1404.

The signal post-processor 1404 performs processing such as logarithmic conversion, frame correlation, gamma correction, contrast adjustment and sharpness filtering on the interference light data transmitted from the FIFO memory unit 1403, and outputs the resulting data to an image construction unit 1405.

At the image construction unit 1405, streams of interference light data in the scanning units (line units) of the optical path length of the reference mirror are converted into video signals. Based on the video signals, tomographic images to be displayed on the LCD monitor 1227 are constructed.

6. Processing at the A/D Converter 1213 and Signal Processor 1214

Figure 15:
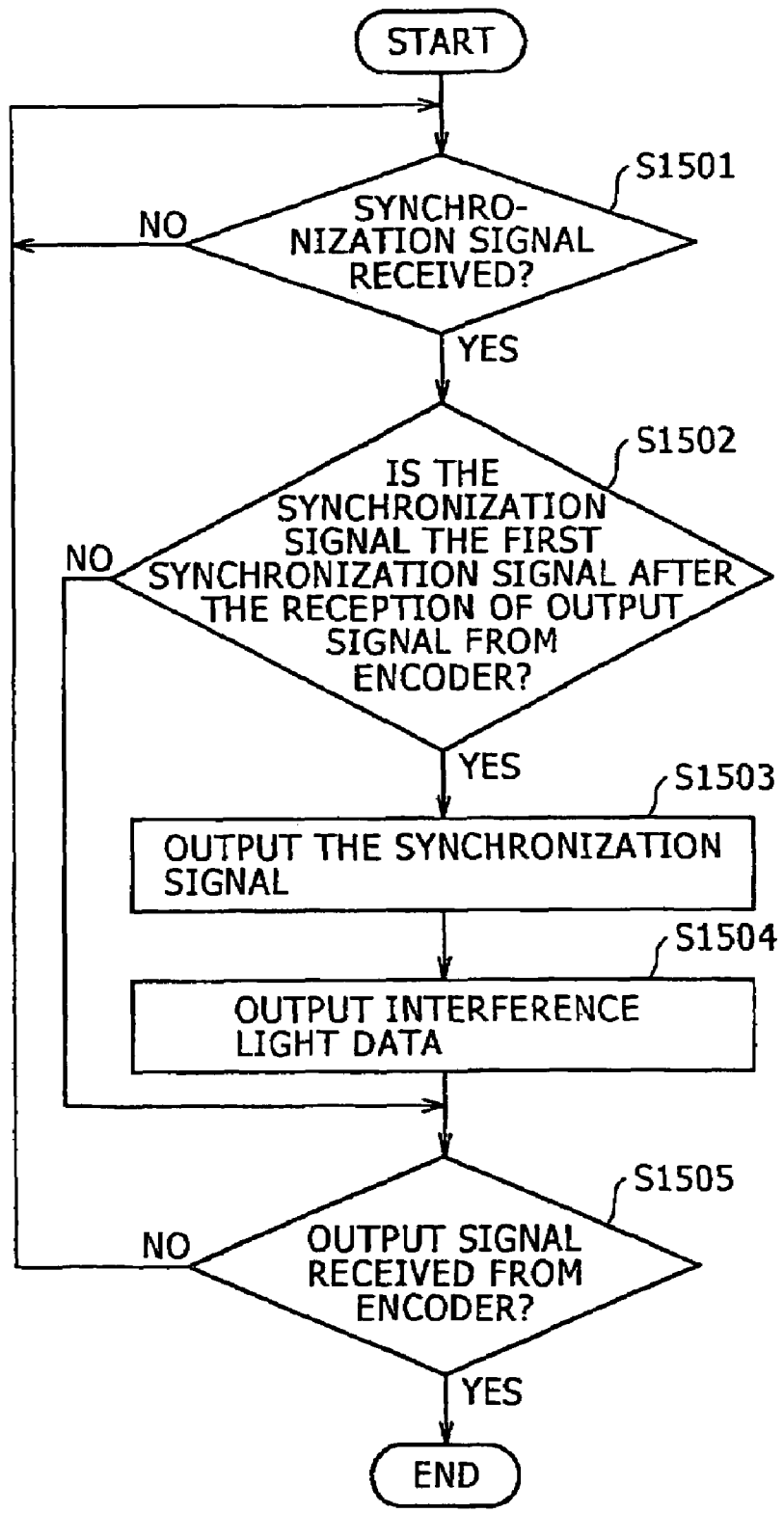
FIG. 15 is a flow chart illustrating operational aspects associated with processing at an A/D converter and signal processor during intravascular OCT.

The processing at the A/D converter 1213 and signal processor 1214 during intravascular OCT by the OCT imaging system 1200 is described below with reference to FIG. 15. Whenever the synchronization signal selector 1402 receives an output pulse from the encoder 1206, the processing shown in FIG. 15 is started.

In step S1501, a determination is made as to whether or not the synchronization signal selector 1402 has received a synchronization signal from the synchronization signal generator 1401. If no synchronization signal has been received yet, the process waits until a synchronization signal is received. When a synchronization signal is received, the process advances to step S1502.

In step S1502, a determination is made as to whether or not the synchronization signal received in step S1501 is the first synchronization signal after the output pulse received from the encoder 1206 upon starting the processing.

If the synchronization signal is determined to be the first synchronization signal in step S1502, the process advances to step S1503 in which the synchronization signal so received is outputted to the A/D converter 1213. The process then advances to step S1504.

In step S1504, the A/D converter 1213 uses the synchronization signal as a trigger to produce interference light data, and outputs the interference light data to the FIFO memory unit 1403.

If the synchronization signal is not determined to be the first synchronization signal in step S1502, the process advances to step S1505 without outputting the thus-received synchronization signal to the A/D converter 1213.

In step S1505, the synchronization signal selector 1402 determines whether or not the next output pulse has been received from the encoder 1206. If the next output pulse has not been received yet, the process returns to step S1501. If the next output pulse has been received, the current processing is ended.

7. Specific Example of the Processing at the A/D Converter and Signal Processor

A specific example of the processing at the A/D converter 1213 and the signal processor 1214 is set forth below with reference to FIG. 16 which is a timing chart illustrating when output pulses from the encoder 1206 and the scanning cycle of the optical path length are out of synchronization.

Figure 16:
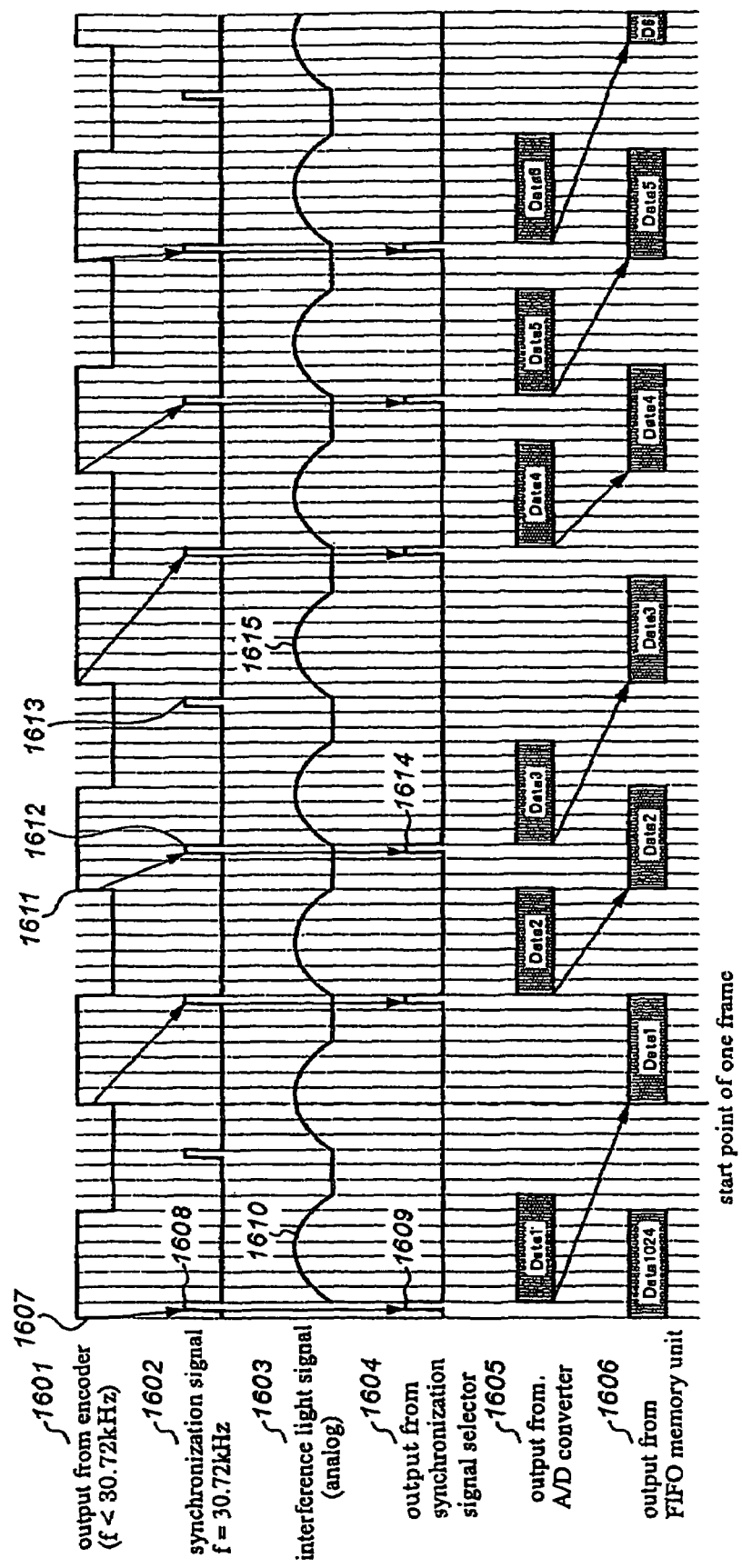
FIG. 16 is a timing chart illustrating when output pulses from an encoder and a scanning cycle of the optical path of a reference mirror are out of synchronization.

FIG. 16 shows a timing 1601 of output pulses from the encoder 1206, a timing 1602 of synchronization signals generated at the synchronization signal generator 1401, a timing 1603 of interference light signals to be inputted to the A/D converter 1213, and a timing 1604 of synchronization signals to be selectively outputted at the synchronization signal selector 1402. In addition, the timing chart shows a timing of interference light data 1605 produced at the A/D converter 1213, and a timing of interference light data 1606 to be read from the FIFO memory unit 1403.

As illustrated in FIG. 16, first a rise of an output pulse at the encoder 1206 (1607). After the rise (1607), upon receipt of a synchronization signal (1608) first produced and outputted at the synchronization signal generator 1401, the synchronization signal selector 1402 outputs the synchronization signal (1609) to the A/D converter 1213. At the A/D converter 1213, the synchronization signal received from the synchronization signal selector 1402 is used as a trigger to subject an interference light signal (1610) to A/D conversion to produce interference light data (Data 1). The interference light data (Data 1) are then stored in the FIFO memory unit 1403. Data 1 stored in the FIFO memory unit 1403 are read in synchronization with an output pulse from the encoder 1206.

In the OCT imaging system according to this embodiment, the scanning cycle of the optical path length from the optical probe 1201 is set shorter than the output cycle of output pulses from the encoder 1206. Thus, in some instances, subsequent to a rise (1611) of an output pulse at the encoder 1206, two synchronization signals (1612, 1613) may be outputted from the synchronization signal generator 1401. In such a case, the first synchronization signal (1612) is selected at the synchronization signal selector 1402, and is outputted to the A/D converter 1213 (1614). On the other hand, the second synchronization signal (1613) is not selected at the synchronization signal selector 1402, and therefore, is not outputted to the A/D converter 1213. As a result, an interference light signal (1615) inputted to the A/D converter 1213 subsequent to the reception of the second synchronization signal (1613) at the synchronization signal selector 1402 is not subjected to A/D conversion and is thinned out.

As is evident from the above description, the OCT imaging system according to this embodiment makes it possible to produce interference light data in accordance with the rotation cycle of the probe in radial scanning even when no synchronization is achieved between the rotation cycle of the probe in the radial scanning and the scanning cycle of the reference optical path length. In other words, it becomes possible to produce interference light data after thinning out any extra interference light signals inputted beyond the number of output pulses from the encoder.

As a result, it is possible to eliminate an inconvenience associated with other known systems involving a tomographic image being displayed blurred in the circumferential direction or being displayed while slowly turning.

Third Embodiment

The above-described second embodiment describes application of the disclosed subject matter to the OCT imaging system. However, the present invention is not limited specifically to OCT imaging systems as it can also be applied to OCT imaging systems making use of a wavelength swept light source. A description will hereinafter be made about applying the disclosure here to an OCT imaging system making use of a wavelength swept light source.

1. Measurement Principle of OCT Imaging System Making Use of a Wavelength Swept Light Source Initially, a brief description is set forth of the measurement principle of the OCT imaging system making use of a wavelength swept light source. The OCT imaging system making use of a wavelength swept light source and the OCT imaging system described above as the second embodiment are basically the same in measurement principle as shown in FIGS. 10 and 11 in that they make use of optical interference. Accordingly, the description which follows primarily discusses differences between the OCT imaging system in this third embodiment and the system described above as the second embodiment.

It is the light source that is different in measurement principle from the OCT imaging system of the second embodiment. First, these OCT imaging systems are thus different in coherent length. More specifically, a light source capable of emitting low-coherence light of from 10 μm to 20 μm or so in coherence length is used in the OCT imaging system of the second embodiment, while a light source having a coherence length of from 4 mm to 10 mm or so is used in the OCT imaging system making use of a wavelength swept light source.

One reason for the above-mentioned difference is that the range of the examinable range in the direction of the depth of a biotissue is dependent on the movable range of the reference mirror in the OCT imaging system as the second embodiment, but is dependent on the coherence length in the OCT imaging system making use of a wavelength swept light source. To encompass the entire range in the direction of the depth of a biotissue such as a blood vessel, a light source having a relatively long coherence length is used in the OCT imaging system making use of a wavelength swept light source.

A second difference in their light sources resides in that in the case of the OCT imaging system making use of a wavelength swept light source, light beams having different wavelengths are continuously irradiated.

In the OCT imaging system according to the second embodiment, the extraction of reflected light from individual points in the direction of the depth of the biotissue is achieved by movements of the reference mirror, and the resolution in the direction of the depth of the measurement target is dependent on the coherent length of irradiated light. The OCT imaging system making use of a wavelength swept light source, on the other hand, is characterized in that light is irradiated while continuously varying its wavelength and the intensities of reflected light from individual points in the direction of the depth of the biotissue are determined based on differences in the frequency component of interference light.

Taking the frequency (the inverse of the wavelength) of scanning light as a time function represented by Equation 1, the intensity of interference light can generally be expressed by a time function represented by Equation 2.

$$f(t) = f\alpha + \Delta ft \qquad \text{(Equation 1)}$$

$$I(t) = A + B\cos(C\Delta x(f\alpha + \Delta ft)) \qquad \text{(Equation 2)}$$

where Δx: optical path difference between the reference light and the target light,
Δf the rate of a change in frequency in unit time, and
A, B, C: constants.

As appreciated from Equation 2, the frequency component in the time-dependent change in the intensity I(t) of reference light is expressed by the optical path difference Δx and the rate Δf of a change in frequency by frequency scanning. Accordingly, the intensity of interference light for each optical path difference can be determined provided that the frequency component of the interference light is known, and signals for one line can be obtained by a single cycle of wavelength sweep.

As a consequence, the time required for acquiring signals for one line can be shortened, and further, the imaging depth can be made greater.

Figure 17:
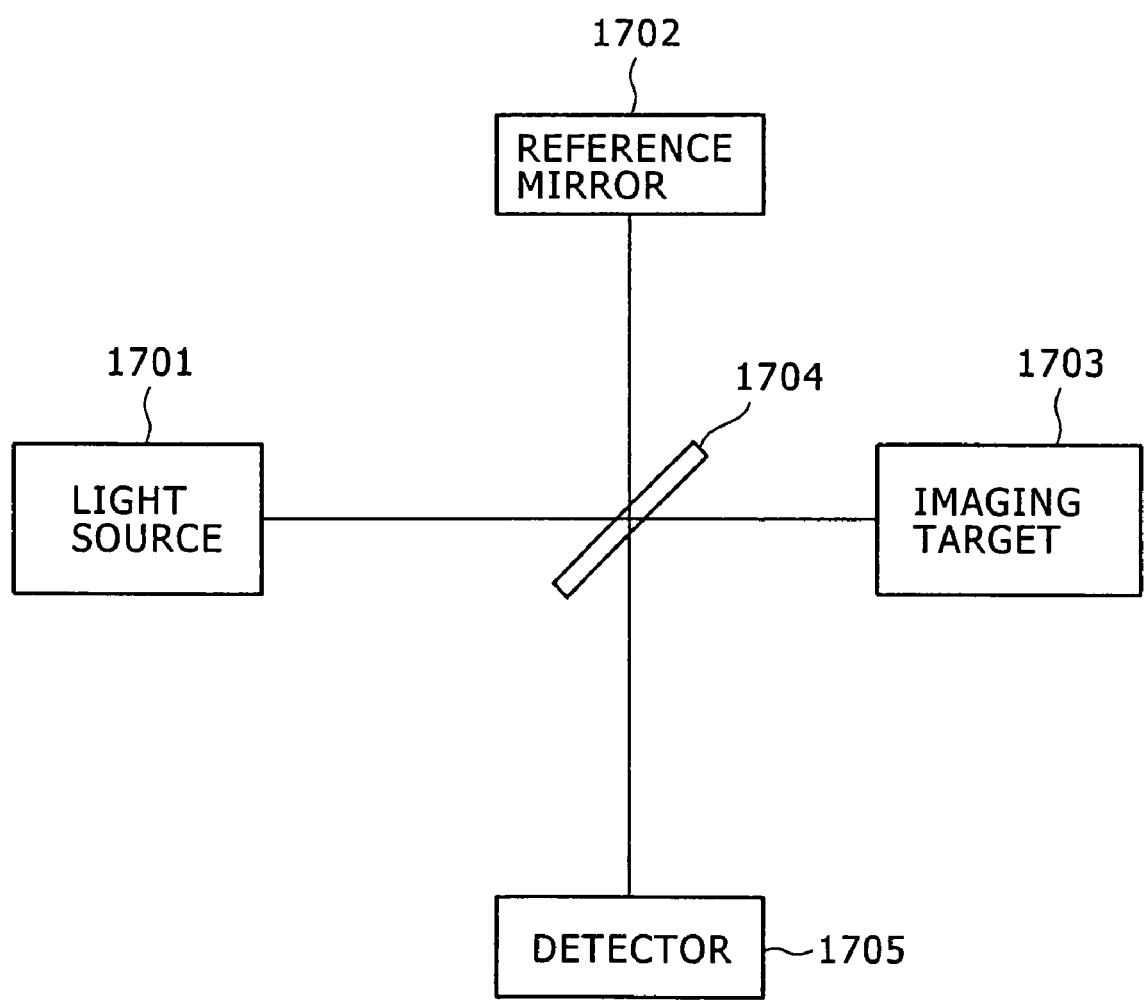
FIG. 17 is a block diagram illustrating the basic principle of an OCT imaging system according to a third embodiment, which makes use of a wavelength swept light source.

A schematic illustration of the basic principle of an OCT imaging system making use of a wavelength swept light source is illustrated in FIG. 17. In this illustrated embodiment, the light source 1701 is a swept laser.

Light beams, which have been successively outputted from the light source 1701 and have different wavelengths, are each split at a beam splitter 1704, and the thus-split light beams then travel toward a reference mirror 1702 (i.e., reference optical path) and toward an imaging target 1703 (i.e., sample optical path), respectively. At this time, reflected light which is returning from the side of the imaging target 1703 includes light reflected on the surface of the imaging target, light reflected at shallow points in the imaging target, and light reflected at deep points in the imaging target.

By subjecting observed reference light to frequency resolution at a detector 1705 as mentioned above, information on a structure at a particular position in the direction of the depth of the measuring target can be visualized. As a result, data for one line can be obtained by a single cycle of wavelength sweep, thereby making it possible to construct a tomographic image.

As the light outputted from the light source 1701 is of from 4 to 10 mm or so in coherence length, it is possible to encompass the entire examination range in the direction of the depth of the imaging target. It is, therefore, unnecessary to move the reference mirror, so that the reference mirror 1702 is arranged fixedly at a constant distance. Moreover the reference mirror is not indispensable in this embodiment. A turned optical fiber, which can return back the light, may be set at the distal end of the reference optical path instead of the reference mirror.

Because it is unnecessary to mechanically move the reference mirror as mentioned above, the OCT imaging system making use of a wavelength swept light source, in comparison with the OCT imaging system according to the second embodiment, requires a shorter time for acquiring signals for one line and can raise the frame rate. As opposed to a maximum frame rate of 15 fr/s (frames/second) in the OCT imaging system according to the second embodiment, the frame rate of the OCT imaging system making use of a wavelength swept light source is as high as from 30 to 200 fr/s or so.

In the case of an OCT imaging system, irrespective of whether or not it makes use of a wavelength swept light source, blood is supposed to be eliminated upon diagnosis so that absorption of light by blood cell components can be avoided to acquire good images. A low frame rate, therefore, requires the elimination of blood for a longer time. This, however, can lead to problems from the clinical standpoint. In the case of an OCT imaging system making use of a wavelength swept light source, images can be acquired over 30 mm or longer in the axial direction of a blood vessel by elimination of blood for several seconds, thereby reducing such clinical concerns.

Figure 18:
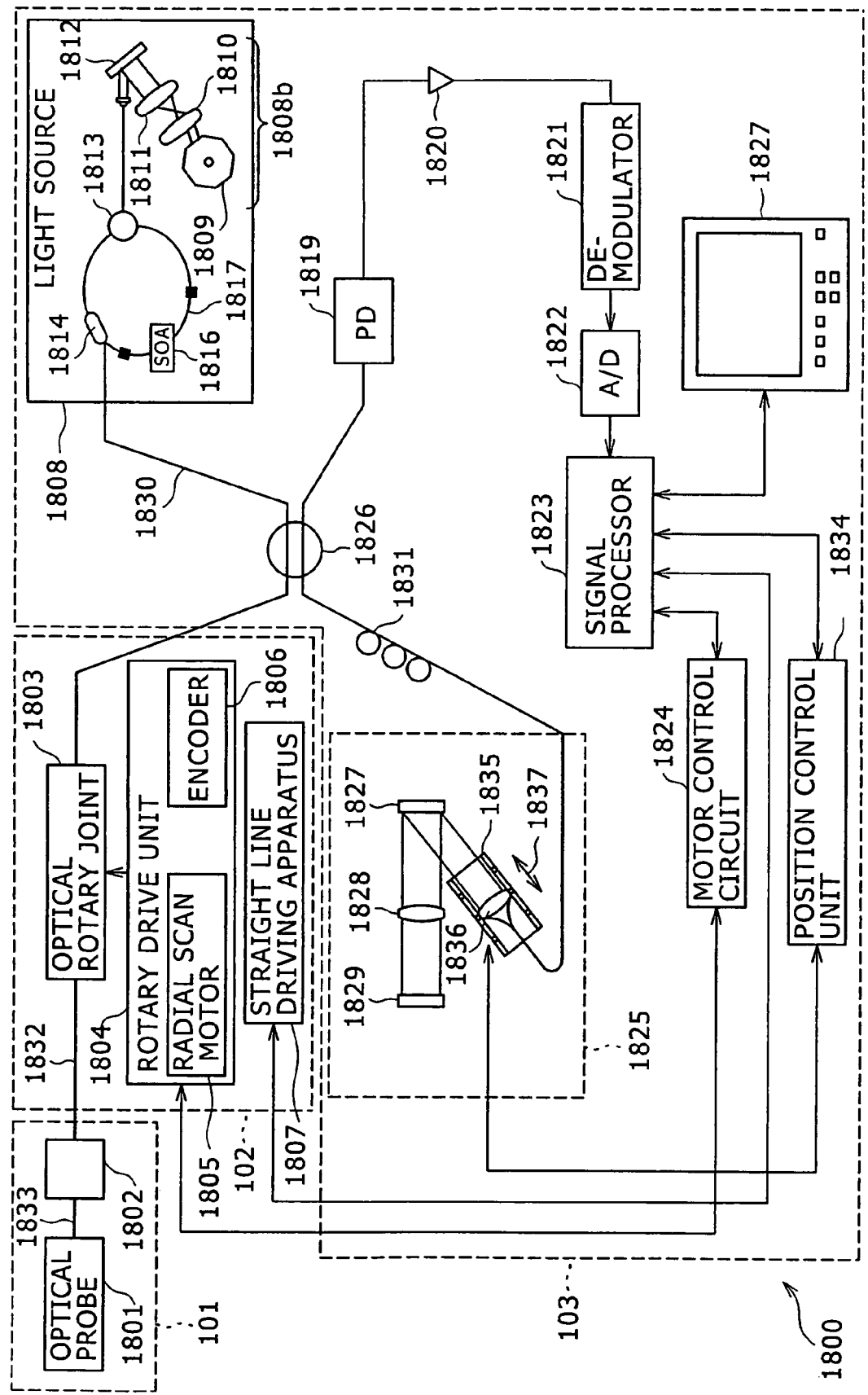
FIG. 18 is a block diagram illustrating functional aspects of the OCT imaging system making use of a wavelength swept light source.

2. Aspects and Features of OCT Imaging System Making Use of Wavelength Swept Light Source Features and aspects of the OCT imaging system 1800 making use of a wavelength swept light source are schematically shown in FIG. 18. The description which follows primarily describes differences in the OCT imaging system making use of a wavelength swept light source relative to the second embodiment described above.

The OCT imaging system making use of a wavelength swept light source includes a light source 1808, with a swept laser used as the light source 1808. This swept laser 1808 is a kind of extended-cavity laser, which includes an optical fiber 1817 and a polygon scanning filter 1808b. The optical fiber 1817 is connected in the form of a ring with a semiconductor optical amplifier (SOA) 1816.

Light outputted from the SOA 1816 advances through the optical fiber 1817, and enters the polygon scanning filter 1808b. Subsequent to wavelength selection through the polygon scanning filter 1808b, the resulting light is amplified at the SOA 1816 and is finally outputted from a coupler 1814.

The polygon scanning filter 1808b selects a wavelength by a combination of a diffraction grating 1812, which separates light into a spectrum, and a polygon mirror 1809. The light which has been separated into the spectrum by the diffraction grating 1812 is condensed on a facet of the polygon mirror 1809 by two lenses (1810, 1811). As a result, only light of a wavelength crossing at a right angle with the polygon mirror 1809 returns on the same light path and is outputted from the polygon scanning filter 1808b. By rotating the mirror 1809, time sweeping of wavelengths is performed.

As an example of the polygon mirror 1809, a 32-sided polygonal mirror can be used, and its rotational speed can be 50,000 rpm or so. By the unique wavelength-sweeping system making the combined use of the polygon mirror 1809 and the diffraction grating 1812, high-speed and high-output wavelength sweeping is feasible.

The light of the swept laser 1808, which has been outputted from the coupler 1814, impinges on a proximal end of a first single mode fiber 1830, and is transmitted toward its distal end face. At an optical coupler 1826 arranged midway along the first single mode fiber 1830, the first single mode fiber 1830 is optically coupled with a second single mode fiber 1831. Therefore, the light transmitted through the first single mode fiber 1830 is split into two by the optical coupler 1826 and the resulting two beams of light are transmitted further.

On the side of a more distal end of the first single mode fiber 1830 than the optical coupler 1826, an optical rotary joint 1803 is arranged to connect a non-rotatable block and a rotatable block with each other such that light can be transmitted.

Further, an optical-probe connector 1802 is detachably connected to a distal end of a third single mode fiber 1832 in the optical rotary joint 1803. Via the connector 1802, the light from the light source 1808 is transmitted to a fourth single mode fiber 1833, which is inserted in an optical probe 1801 and is rotationally drivable.

The transmitted light is irradiated from a distal end side of the optical probe 1801 toward a surrounding biotissue of a body cavity while performing radial scanning. A portion of reflected light scattered on a surface or interior of the biotissue is collected by the optical probe 1801, and returns to the side of the first single mode fiber 1830 through the same optical path (sample optical path). A portion of the thus-collected, reflected light is transferred by the optical coupler 1826 to the side of the second single mode fiber 1830, and is introduced into a photodetector (for example, photodiode 1819) from an end of the second single mode fiber 1831.

It is to be noted that the rotatable block side of the optical rotary joint 1803 is rotationally driven by a radial scan motor 1805. Further, rotation angles of the radial scan motor 1805 are detected by an encoder 1806 and outputted as an output pulse. The optical rotary joint 1803 is provided with a linear drive unit 1807 that, based on an instruction from a signal processor 1823, controls a movement of the catheter section 101 in the direction of its insertion.

On the side of a more distal end of the second single mode fiber 1831 than the optical coupler 1826 (i.e., reference optical path), an optical path length (OPL) varying mechanism 1825 is arranged to finely adjust the optical path length of reference light.

This OPL varying mechanism 1825 is provided with a an OPL varying means for slightly varying the optical path length by a length equivalent to a variation in the length of a new optical probe to absorb the variation when the new optical probe is used as a replacement.

The second single mode fiber 1831 and a collimator lens 1836 are mounted on a single axis stage 1835 movable in the direction of an optical axis of the collimator lens 1836 as indicated by an arrow 1837, thereby forming the OPL varying mechanism.

Described specifically, the single axis stage 1835 forms the OPL varying mechanism having a variable OPL range just enough to absorb a variation in the optical path length of a new optical probe when the optical probe 1801 is replaced by the new optical probe. In addition, the single axis stage 1835 is also equipped with a function as an adjustment means for adjusting an offset. Even when the distal end of the optical probe 1801 is not in close contact with a surface of the biotissue, for example, the optical probe can still be set in such a state as interfering from a position on the surface of the biotissue by slightly varying the optical path length with the single axis stage 1835.

The light finely adjusted in optical path length by the OPL varying mechanism 1825 is returned by the reference mirror 1829 and combined with the light, which has returned from the sample optical path, at the optical coupler 1826 arranged midway along the second single mode fiber 1831, and the combined light is received at the photodiode 1819.

The light received at the photodiode 1819 is photoelectrically converted, amplified by an amplifier 1820, and then inputted into a demodulator 1821. At the demodulator 1821, demodulation processing is performed to extract only the signal portion of the interfered light, and the output of the demodulator 1821 is inputted into an A/D converter 1822.

At the A/D converter 1822, interference light signals are sampled at 180 MHz as much as for 2,048 points to produce digital data (interference light data) for one line. It is to be noted that the setting of the sampling frequency at 180 MHz is attributed to the premise that approximately 90% of the cycle of wavelength sweep (12.5 μsec) be extracted as digital data at 2,048 points when the wavelength sweep repetition frequency is set at 40 kHz. The sampling frequency should, therefore, not be limited specifically to the above-described value.

The interference light data in the light unit, which have been produced at the A/D converter 1822, are inputted into a signal processor 1823. At this signal processor 1823, the interference light data are frequency-resolved by FFT (Fast Fourier Transform) to produce data in the direction of the depth. These data are then coordinate-transformed to construct tomographic images at respective positions in the blood vessel. The tomographic images are then outputted at a predetermined frame rate to an LCD monitor 1827.

It is to be noted that the signal processor 1823 is connected with a position control unit 1834. The signal processor 1823 performs control of the position of the single axis stage 1835 via the position control unit 1834. In addition, the signal processor 1823 is also connected with a motor control circuit 1824 to control rotational drive by the radial scan motor 1805.

3. Features of Catheter Section

The overall construction of the catheter section 101 and the construction of its distal end portion are similar to those of the catheter section in the OCT imaging device described above as the second embodiment with reference to FIG. 13. A detailed description of the catheter section 101 is thus not repeated here.

4. Features of Signal Processor

Figure 19:
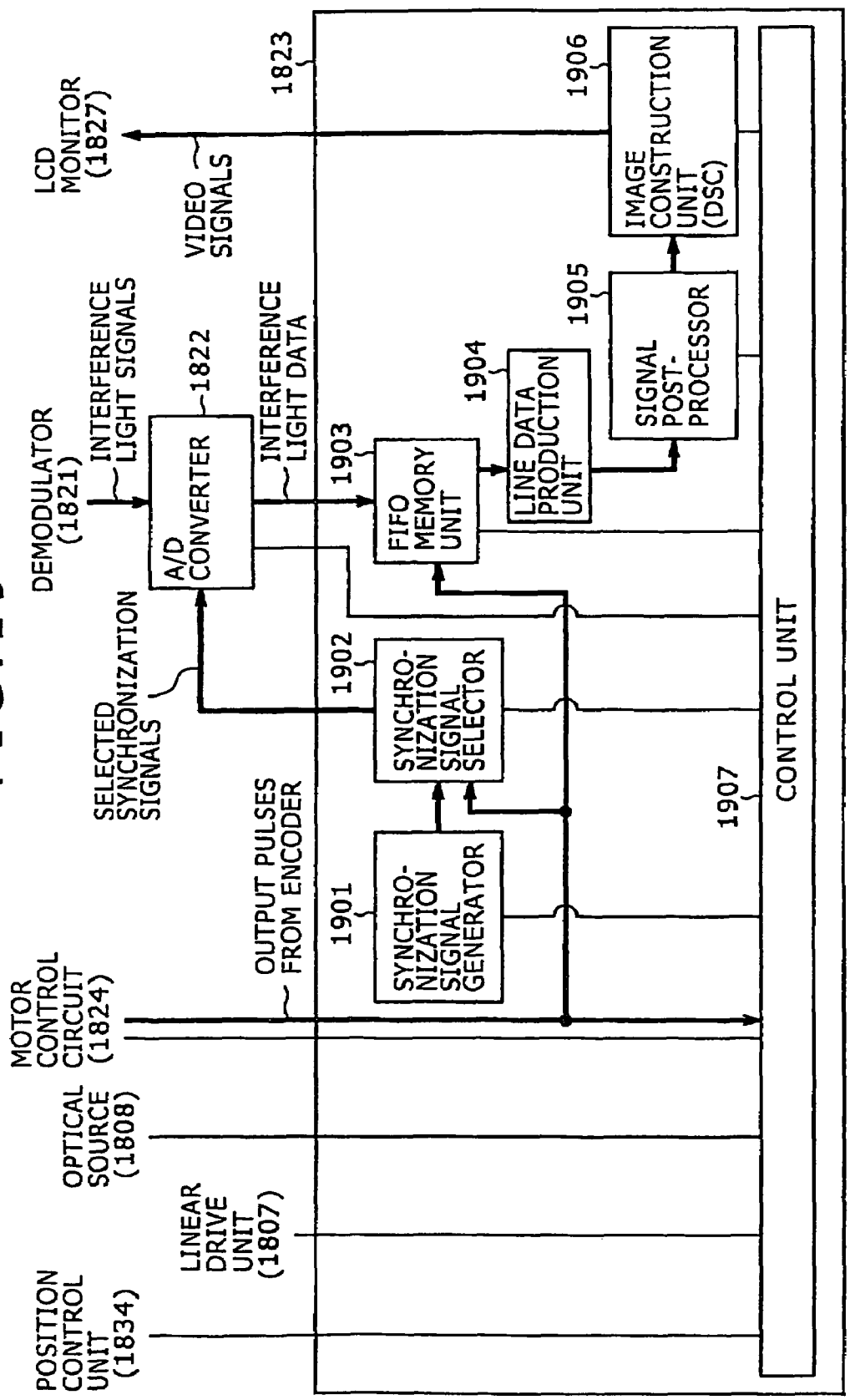
FIG. 19 is a block diagram depicting aspects of a signal processor in the OCT imaging system making use of a wavelength swept light source.

Features associated with the signal processor 1823 in the OCT imaging system 1800 making use of a wavelength swept light source are shown in FIG. 19. The signal processor 1823 includes a main control unit 1907 which systematically controls the entirety of the OCT imaging system 1800 making use of a wavelength swept light source.

Designated at numeral 1901 is a synchronization signal generator (i.e., a generation unit). This synchronization signal generator 1901 generates a synchronization signal which is in synchronization with the wavelength sweep cycle of the light source 1808, and outputs the synchronization signal to a synchronization signal selector (i.e. a selection unit) 1902. Predetermined sets of the wavelength sweep cycle of the light source 1808 for generating a single frame image are set shorter than a predetermined set of the output cycle of output pulses from the encoder 1806 for generating a single frame image. Set forth below is a brief description of the wavelength sweep cycle being set shorter than the output cycle of output pulses.

The synchronization signal selector 1902 receives output pulses from the encoder 1806 and synchronization signals outputted from the synchronization signal generator 1901. Among the synchronization signals so received, only the synchronization signals received first after the rise of the respective output pulses at the encoder 1806 are selected, and the thus-selected synchronization signals are outputted to the A/D converter 1822.

More specifically, the synchronization signal selector 1902 functions such that, when plural synchronization signals have been received after the rise of each output pulse at the encoder 1806 until the rise of the subsequent output pulse at the encoder 1806, only the first synchronization signal is selected and the remaining synchronization signal or signals are thinned out.

From the synchronization signal selector 1902, as many synchronization signals are outputted as output pulses from the encoder 1806. The synchronization signal selector 1902 is designed to monitor the rise of each output pulse at the encoder 1806. The present invention is, however, not limited specifically to the monitoring of the rise of each output pulse. The synchronization signal selector 1902 may be designed, for example, to monitor the fall of each output pulse. As a matter of fact, the synchronization signal selector 1902 may be designed in any construction insofar as it outputs only one pulse as a synchronization signal during one cycle of output pulses from the encoder 1806.

Each synchronization signal outputted from the synchronization signal selector 1902 is inputted to the A/D converter 1822. At the A/D converter 1822, the synchronization signal inputted from the synchronization signal selector 1902 is used as a trigger to sample interference light signals for as much as 2,048 points, thereby producing one line of digital data (interference light data). The sampling frequency is a value of approximately 90% of the cycle of wavelength be extracted as digital data at 2,048 points.

Each line unit of interference light data produced at the A/D converter 1822 is outputted to an FIFO memory unit 1903.

The FIFO memory unit 1903 once stores the interference light data inputted from the A/D converter 1822. In synchronization with an output pulse from the encoder 1806, the interference light data are read and inputted to a line data production unit 1904. The interference light data are subjected to wavelength resolution by FFT processing. One line of depth data are produced, and are outputted to a signal post-processor 1905.

The signal post-processor 1905 performs processing such as frame correlation, gamma correction, contrast adjustment and sharpness filtering on the interference light data transmitted from the FIFO memory unit 1903, and outputs the resulting data to an image construction unit 1906.

At the image construction unit 1906, streams of depth data in wavelength sweeping units (line units) are converted into video signals. Based on the video signals, tomographic images to be displayed on the LCD monitor 1827 are constructed.

5. Processing at the A/D Converter 1822 and Signal Processor 1823

Figure 20:
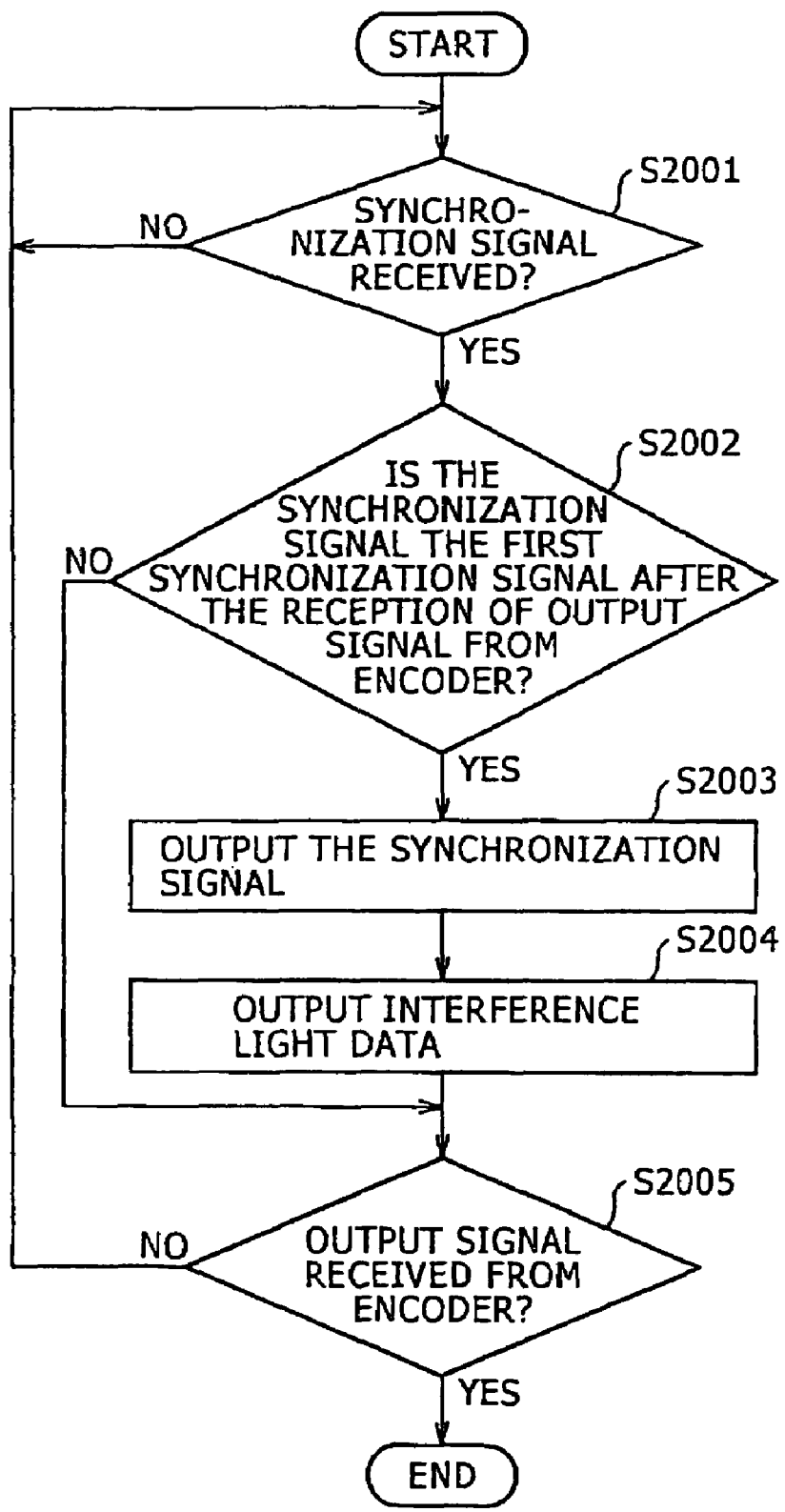
FIG. 20 is a flow chart showing aspects of the processing at an A/D converter and signal processor during intravascular OCT.

With reference to FIG. 20, the following is a description of the processing at the A/D converter 1822 and signal processor 1823 by the OCT imaging system 1800 making use of a wavelength swept light source for an intravascular diagnosis.

Whenever the synchronization signal selector 1902 receives an output pulse from the encoder 1806, the processing shown in FIG. 20 is started.

In step S2001, a determination is made as to whether or not the synchronization signal selector 1902 has received a synchronization signal from the synchronization signal generator 1901. If no synchronization signal has been received yet, the process waits until a synchronization signal is received. Once a synchronization signal is received, the process advances to step S2002.

In step S2002, a determination is made as to whether or not the synchronization signal received in step S2001 is the first synchronization signal after the output pulse received from the encoder 1806 upon starting the processing.

If the synchronization signal is determined to be the first synchronization signal in step S2002, the process advances to step S2003, in which the synchronization signal so received is outputted to the A/D converter 1822. The process then advances to step S2004.

In step S2004, the A/D converter 1822 uses the synchronization signal as a trigger to produce interference light data, and outputs the interference light data to the FIFO memory unit 1903.

If the synchronization signal is not determined to be the first synchronization signal in step S2002, the process advances to step S2005 without outputting the thus-received synchronization signal to the A/D converter 1822.

In step S2005, the synchronization signal selector 1902 determines whether or not the next output pulse has been received from the encoder 1806. If the next output pulse has not been received yet, the process returns to step S2001. If the next output pulse has been received, on the other hand, the current processing is ended.

6. Specific Example of the Processing at the A/D Converter and Signal Processor

Set forth below is a description of a specific example of the processing at the A/D converter 1822 and the signal processor 1823, with reference to the illustration in FIG. 21.

Figure 21:
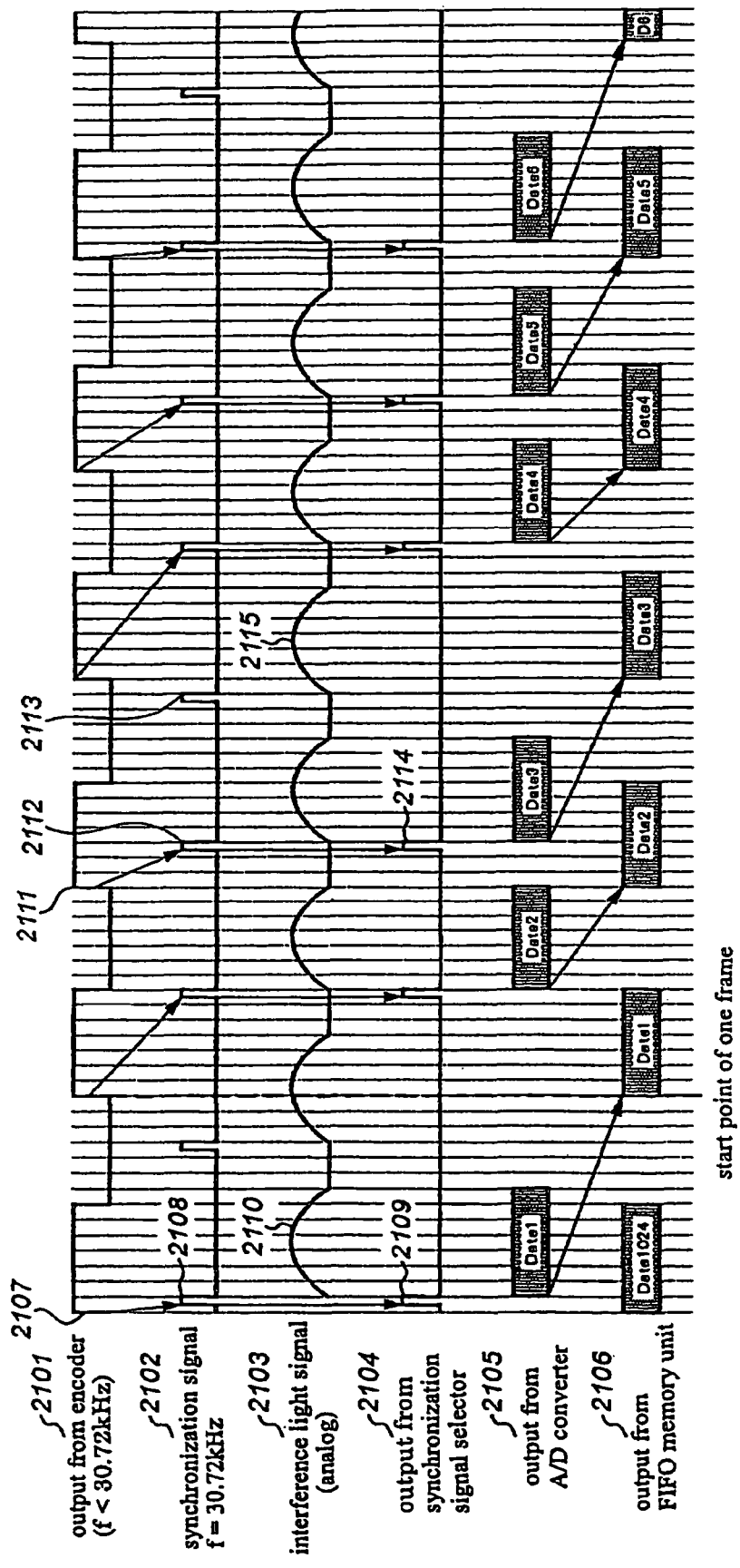
FIG. 21 is a timing chart illustrating when output pulses from an encoder and a scanning cycle of the optical path of a reference mirror are out of synchronization.

FIG. 21 is a timing chart illustrating when the output pulses from the encoder 1806 and the wavelength sweep cycle of the light source 1808 are out of synchronization. FIG. 21 illustrates a timing 2101 of output pulses from the encoder 1806, a timing 2102 of synchronization signals generated at the synchronization signal generator 1901, a timing 2103 of interference light signals to be inputted to the A/D converter 1822, and a timing 2104 of synchronization signals to be selectively outputted at the synchronization signal selector 1902. The timing chart also shows a timing of interference light data 2105 produced at the A/D converter 1822 and a timing of interference light data 2106 to be read from the FIFO memory unit 1903.

As illustrated in FIG. 21, upon receipt of a synchronization signal (2108) first produced and outputted at the synchronization signal generator 1901 after a rise (2107) of an output pulse at the encoder 1806, the synchronization signal selector 1902 outputs the synchronization signal (2109) to the A/D converter 1822. At the A/D converter 1822, the synchronization signal received from the synchronization signal selector 1902 is used as a trigger to subject an interference light signal (2110) to A/D conversion to produce interference light data (Data 1). The interference light data (Data 1) are then stored in the FIFO memory unit 1903. Data 1 stored in the FIFO memory unit 1903 are read in synchronization with an output pulse from the encoder 1806.

In the OCT imaging system making use of a wavelength swept light source according to this embodiment, the cycle of wavelength sweep is set shorter than the output cycle of output pulses from the encoder 1806. Subsequent to a rise (2111) of an output pulse at the encoder 1806, two synchronization signals (2112, 2113) may be outputted from the synchronization signal generator 1901 in some instances.

In such a case, the first synchronization signal (2112) is selected at the synchronization signal selector 1902, and is outputted to the A/D converter 1822 (2114). The second synchronization signal (2113) is not selected at the synchronization signal selector 1902 and, therefore, is not outputted to the A/D converter 1822. As a result, an interference light signal (2115) inputted to the A/D converter 1822 subsequent to the reception of the second synchronization signal (2113) at the synchronization signal selector 1902 is not subjected to A/D conversion and is thinned out.

As is evident from the above description, the OCT imaging system making use of a wavelength swept light source according to this embodiment makes it possible to produce interference light data in accordance with the rotation cycle of the probe during radial scanning even when no synchronization is achieved between the rotation cycle of the probe in the radial scanning needed for generating a single frame of an image and the cycle of wavelength sweep needed for generating the single frame of the image. In other words, it becomes possible to produce interference light data after thinning out any extra interference light signals inputted beyond the number of output pulses from the encoder.

As a result, it is possible to eliminate inconveniences such as associated with other known systems in which a tomographic image may be displayed blurred in the circumferential direction or may be displayed while slowly turning.

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An image diagnostic system comprising:
   a radial scanner;
   a probe positionable in a body cavity and configured to repeatedly transmit signals and acquire line units of signals reflected from biotissue surrounding the body cavity with the radial scanner;
   an encoder configured to generate output signals corresponding to rotational angles of the probe upon performing the radial scanning;
   a control system connected to the probe to receive the acquired reflected line units of signals and produce digital data based on the acquired reflected line units of signals and to construct a tomographic image of the body cavity and the biotissue surrounding the body cavity on the basis of the digital data; and
   a display unit configured to display the tomographic image;
   the control system comprising:
      a generation unit configured to output synchronization signals in synchronization with a timing of acquisition cycles of the acquired signals, the synchronization signals having a higher frequency than the output signals;
      a selection unit connected to the generation unit to receive the synchronization signals from the generation unit and the output signals generated by the encoder, the selection unit selecting and outputting one of the synchronization signals which is first received subsequent to reception of one of the output signals generated by the encoder; and
      a conversion unit configured to convert the acquired reflected line units of signals into digital line data and output the digital line data responsive to successive inputs of the synchronization signals selected by the selection unit for use in constructing the tomographic image.

2. The image diagnostic system according to claim 1, further comprising:
   a holding unit configured to temporarily hold the digital data outputted from the conversion unit; and
   wherein the digital data held in the holding unit are read in synchronization with the output signals to construct the tomographic image of the body cavity and the surrounding biotissue.

3. The image diagnostic system according to claim 1, wherein the probe is an ultrasonic transducer configured to transmit and receive ultrasounds, and the digital data are produced based on waves reflected from the biotissue surrounding the body cavity and received through the probe.

4. The image diagnostic system according to claim 1, wherein the probe is connected to a light source configured to output light for imaging, with the probe transmitting and receiving the light, the digital data being produced based on interference light between light reflected from the biotissue surrounding the body cavity and received through the probe and reference light outputted from the light source.

5. The image diagnostic system according to claim 1, wherein the probe is connected to a light source which outputs a wavelength-swept light source.

6. An image diagnostic apparatus adapted to be connected to a mechanism comprising a probe which repeatedly transmits signals into a body cavity and acquires line units of signals reflected by biotissue surrounding the body cavity to perform radial scanning within the body cavity, and also adapted to be connected to an encoder configured to generate output signals corresponding to rotational angles of the probe upon performing the radial scanning, the image diagnostic apparatus comprising:
   a control system configured to produce digital data based on the acquired reflected line units of signals and to construct a tomographic image of the body cavity and the biotissue surrounding the body cavity on the basis of the digital data, the control system comprising:
      a generation unit configured to generate and output synchronization signals in synchronization with a timing of acquisition cycles of the acquired signals, the synchronization signals having a higher frequency than the output signals generated by the encoder;
      a selection unit connected to the generation unit to receive successive ones of the synchronization signals from the generation unit, the selection unit receiving more than one synchronization signal subsequent to receipt of one output signal generated by the encoder and prior to receipt of an immediately following output signal generated by the encoder, the selection unit being configured to select and output only the synchronization signal which is first received subsequent to receipt of the one output signal and prior to receipt of the immediately following output signal; and
      a conversion unit configured to convert the acquired reflected line units of signals into digital line data and output the digital line data responsive to successive inputs of the synchronization signals selected by the selection unit.

7. The image diagnostic apparatus according to claim 6, further comprising a display unit connected to the control unit and configured to display the tomographic image produced from the digital data.

8. The image diagnostic apparatus according to claim 6, further comprising:
   a holding unit configured to temporarily hold the digital data outputted from the conversion unit; and
   wherein the digital data held in the holding unit are read in synchronization with the output signals to construct the tomographic image of the body cavity and the surrounding biotissue.

9. An image diagnostic apparatus adapted to be connected to a probe which repeatedly transmits signals into a body cavity and acquires line units of signals reflected by biotissue surrounding the body cavity to perform radial scanning within the body cavity, and also adapted to be connected to an encoder configured to generate output signals corresponding to rotational angles of the probe upon performing the radial scanning, the image diagnostic apparatus comprising:
   a control system configured to produce digital data based on the acquired reflected line units of signals and to construct a tomographic image of the body cavity and the biotissue surrounding the body cavity on the basis of the digital data; and
   a display unit configured to display the tomographic image,
   the control system comprising:
      a generation unit configured to generate and output synchronization signals in synchronization with a timing of acquisition cycles of the line units of signals, the synchronization signals having a higher frequency than the output signals generated by the encoder;
      a selection unit configured to receive the synchronization signals from the generation unit and the output signals generated by the encoder, the selection unit being configured to select and output one of the synchronization signals which is first received subsequent to reception of one of the output signals generated by the encoder; and a conversion unit configured to convert the reflected line units of signals into digital line data and output the digital line data responsive to successive inputs of the synchronization signals selected by the selection unit for use in constructing the tomographic image.

10. The image diagnostic apparatus according to claim 9, further comprising:

a holding unit configured to temporarily hold the digital data outputted from the conversion unit; and wherein the digital data held in the holding unit are read in synchronization with the output signals to construct the tomographic image of the body cavity and the surrounding biotissue.

11. The image diagnostic apparatus according to claim 9, wherein the probe to which the image diagnostic apparatus is adapted to be connected comprises an ultrasonic transducer configured to transmit and receive ultrasounds, and the digital data are produced based on waves reflected from the biotissue surrounding the body cavity and received through the probe.

12. The image diagnostic apparatus according to claim 9, wherein the probe to which the image diagnostic apparatus is adapted to be connected is connected to a light source configured to output light for imaging, with the probe transmitting and receiving the light, the digital data being produced based on interference light between light reflected from the biotissue surrounding the body cavity and received through the probe and reference light outputted from the light source.

13. The image diagnostic apparatus according to claim 12, wherein the probe to which the image diagnostic apparatus is adapted to be connected to a light source adapted to output a wavelength-swept light source.

* * * * *